US008147840B2

(12) United States Patent
Ofek et al.

(10) Patent No.: US 8,147,840 B2
(45) Date of Patent: Apr. 3, 2012

(54) HUMAN IMMUNODEFICIENCY VIRUS (HIV) IMMUNIZATION STRATEGIES EMPLOYING CONFORMATIONALLY-STABILIZED, SURFACE-OCCLUDED PEPTIDES COMPRISING A GP41 2F5 EPITOPE IN ASSOCIATION WITH LIPID

(75) Inventors: Gilad Ofek, Washington, DC (US); **Peter D. K

OTHER PUBLICATIONS

De Rosny, E. et al. (2004) "Binding of the 2F5 monoclonal antibody to native and fusion-intermediate forms of human immunodeficiency virus type 1 gp41: implications for fusion-inducing conformational changes." *J. Virol.* 78:2627-2631.

Eckhart, L. et al. (1996) "Immunogenic presentation of a conserved gp41 epitope of human immunodeficiency virus type 1 on recombinant surface antigen of hepatitis B virus." *J. Gen. Virol.* 77:2001-2008.

Ernst, W. et al. (1998) "Baculovirus surface display: construction and screening of a eukaryotic epitope library." *Nucleic Acids Res.* 26:1718-1723.

Finnegan, C.M. et al. (2002) "Antigenic properties of the human immunodeficiency virus transmembrane glycoprotein during cell-cell fusion." *J. Virol.* 76:12123-12134.

Furuta, R.A. et al. (1998) "Capture of an early fusion-active conformation of HIV-1 gp41." *Nat. Struct. Biol.* 5:276-279.

Grundner, C. et al. (2002) "Solid-phase proteoliposomes containing human immunodeficiency virus envelope glycoproteins." *J. Virol.* 76:3511-3521.

Ho, J. et al. (2002) "Construction of recombinant targeting immunogens incorporating an HIV-1 neutralizing epitope into sites of differing conformational constraint." *Vaccine* 20:1169-1180.

Huang, C.C. et al. (2004) "Structural basis of tyrosine sulfation and $V_H$-gene usage in antibodies that recognize the HIV type 1 coreceptor-binding site on gp120." *PNAS USA* 101:2706-2711.

International Preliminary Report on Patentability from PCT/US2005/016633.

Jones, T.A. et al. (1991) "Improved methods for building protein models in electron density maps and the location of errors in these models." *Acta Crystallogr.* A47:110-119.

Kunert, R. et al. (1998) "Molecular characterization of five neutralizing anti-HIV type 1 antibodies: identification of nonconventional D segments in the human monoclonal antibodies 2G12 and 2F5." *AIDS Res. Hum. Retroviruses* 14:1115-1128.

Kunert, R. et al. (2000) "Stable recombinant expression of the anti HIV-1 monoclonal antibody 2F5 after IgG3/IgG1 subclass switch in CHO cells." *Biotechnol. Bioeng.* 67:97-103.

Kwong, P.D. et al. (1999) "Use of cryoprotectants in combination with immiscible oils for flash cooling macromolecular crystals." *J. Appl. Crystallogr.* 32:102-105.

Kwong, P.D. et al. (2002) "HIV-1 evades antibody-mediated neutralization through conformational masking of receptor-binding sites." *Nature* 420:678-682.

Labrijn, A.F. et al. (2003) "Access of antibody molecules to the conserved coreceptor binding site on glycoprotein gp120 is sterically restricted on primary human immunodeficiency virus type 1." *J. Virol.* 77:10557-10565.

Laskowski, R.A. et al. (1993) "PROCHECK: a program to check the stereochemical quality of rotein structures." *J. Appl. Crystallogr.* 26:283-291.

Liang, X. et al. (1999) "Epitope insertion into variable loops of HIV-1 gp120 as a potential means to improve immunogenicity of viral envelope protein." *Vaccine* 17:2862-2872.

Liao, M. et al. (2000) "Induction of high level of specific antibody response to the neutralizing epitope ELDKWA on HIV-1 gp41 by peptide-vaccine." *Peptides* 21:463-468.

Mascola, J.R. et al. (2002) "Human immunodeficiency virus type 1 neutralization measured by flow cytometric quantitation of single-round infection of primary human T cells." *J. Virol.* 76:4810-4821.

McDonald, I.K. et al. (1994) "Satisfying hydrogen bonding potential in proteins." *J. Mol. Biol.* 238:777-793.

McGaughey, G.B. et al. (2003) "HIV-1 vaccine development: constrained peptide immunogens show improved binding to the anti-HIV-1 gp41 MAb." *Biochemistry* 42:3214-3223.

McRee, D.E. (1999) "XtalView/Xfit—a versatile program for manipulating atomic coordinates and electron density." *J. Struct. Biol.* 125:156-165.

Merritt, E.A. et al. (1997) "[26] raster3D: photorealistic molecular graphics." *Methods Enzymol.* 277:505-524.

Munoz-Barroso, I. et al. (1999) "Role of the membrane-proximal domain in the initial stages of human immunodeficiency virus type 1 envelope glycoprotein-mediated membrane fusion." *J. Virol.* 73:6089-6092.

Muster, T. et al. (1993) "A conserved neutralizing epitope on gp41 of human immunodeficiency virus type 1." *J. Virol.* 67:6642-6647.

Muster, T. et al. (1994) "Cross-neutralizing activity against divergent human immunodeficiency virus type 1 isolates induced by the gp41 sequence ELDKWAS." *J. Virol.* 68:4031-4034.

Nicholls, A. et al. (1991) "Protein folding and association: insights from the interfacial and thermodynamic properties of hydrocarbons." *Proteins: Structure, Function & Genetics* 11:281-296.

Ofek, G. et al. (2004) "Structure and mechanistic analysis of the anti-human immunodeficiency virus type 1 antibody 2F5 in complex with its gp41 epitope." *J. Virol.* 78:10724-10737.

Otwinowski, Z. et al. (1997) "Processing of X-ray diffraction data collected in oscillation mode." *Methods Enzymol.* 276:307-326.

Pantophlet, R. et al. (2003) "Hyperglycosylated mutants of human immunodeficiency virus (HIV) type 1 monomeric gp120 as novel antigens for HIV vaccine design." *J. Virol.* 77:5889-5901.

Parker, C.E. et al. (2001) "Fine definition of the epitope on the gp41 glycoprotein of human immunodeficiency virus type 1 for the neutralizing monoclonal antibody 2F5." *J. Virol.* 75:10906-10911.

Parren, P.W. et al. (1995) "Protection against HIV-1 infection in hu-PBL-SCID mice by passive immunization with a neutralizing human monoclonal antibody against the gp120 CD4-binding site." *AIDS* 9:F1-F6.

Purtscher, M. et al. (1994) "A broadly neutralizing human monoclonal antibody against gp41 of human immunodeficiency virus type 1." *AIDS Res. Hum. Retroviruses* 10:1651-1658.

Purtscher, M. et al. (1996) "Restricted antigenic variability of the epitope recognized by the neutralizing gp41 antibody 2F5." *AIDS* 10:587-593.

Richman, D.D. et al. (2003) "Rapid evolution of the neutralizing antibody response to HIV type 1 infection." *PNAS USA* 100:4144-4149.

Roben, P. et al. (1994) "Recognition properties of a panel of human recombinant Fab fragments to the CD4 binding site of gp120 that show differing abilities to neutralize human immunodeficiency virus type 1." *J. Virol.* 68:4821-4828.

Roederer, M. et al. (1997) "8 color, 10-parameter flow cytometry to elucidate complex leukocyte heterogeneity." *Cytometry* 29:328-339.

Salzwedel, K. et al. (1999) "A conserved tryptophan-rich motif in the membrane-proximal region of the human immunodeficiency virus type 1 gp41 ectodomain is important for Env-mediated fusion and virus infectivity." *J. Virol.* 73:2469-2480.

Saphire, E.O. et al. (2001) "Crystal structure of a neutralizing human IgG against HIV-1: a template for vaccine design." *Science* 293:1155-1159.

Sattentau, Q.J. et al. (1995) "Epitope exposure on functional, oligomeric HIV-1 gp41 molecules." *Virology* 206:713-717.

Schibli, D.J. et al. (2001) "The membrane-proximal tryptophan-rich region of the HIV glycoprotein, gp41, forms a well-defined helix in dodecylphosphocholine micelles." *Biochemistry* 40:9570-9578.

Stiegler, G. et al. (2001) "A potent cross-clade neutralizing human monoclonal antibody against a novel epitope on gp41 of human immunodeficiency virus type 1." *AIDS Res. Hum. Retroviruses* 17:1757-1765.

Stura, E. et al. (1991) "Applications of the streak seeding technique in protein crystallization." *J. Crystal Growth* 110:270-282.

Tian, Y. et al. (2002) "Structure-affinity relationships in the gp41 ELDKWA epitope for the HIV-1 neutralizing monoclonal antibody 2F5: effects of side-chain and backbone modifications and conformational constraints." *J. Peptide Res.* 59:264-276.

Trkola, A. et al. (1995) "Cross-clade neutralization of primary isolates of human immunodeficiency virus type 1 by human monoclonal antibodies and tetrameric CD4-IgG." *J. Virol.* 69:6609-6617.

Trkola, A. et al. (1996) "Human monoclonal antibody 2G12 defines a distinctive neutralization epitope on the gp120 glycoprotein of human immunodeficiency virus type 1." *J. Virol.* 70:1100-1108.

Wei, X. et al. (2003) "Antibody neutralization and escape by HIV-1." *Nature* 422:307-312.

Weiss, R.A. et al. (1985) "Neutralization of human T-lymphotropic virus type III by sera of AIDS and AIDS-risk patients." *Nature* 316:69-72.

Weissenhorn, W. et al. (1997) "Atomic structure of the ectodomain from HIV-1 gp41." *Nature* 387:426-430.

Xiao, Y. et al. (2000) "Epitope-vaccine induces high levels of ELDKWA-epitope-specific neutralizing antibody." *Immunol. Investig.* 29:41-50.

Yang, Z.Y. et al. (2004) "pH-dependent entry of severe acute respiratory syndrome coronavirus is mediated by the spike glycoprotein and enhanced by dendritic cell transfer through DC-SIGN." *J. Virol.* 78:5642-5650.

Zwick, M.B. et al. (2001) "Broadly neutralizing antibodies targeted to the membrane-proximal external region of human immunodeficiency virus type 1 glycoprotein gp41." *J. Virol.* 75:10892-10905.

Zwick, M.B. et al. (2004) "The long third complementarity-determining region of the heavy chain is important in the activity of the broadly neutralizing anti-human immunodeficiency virus type 1 antibody 2F5." *J. Virol.* 78:3155-3161.

* cited by examiner

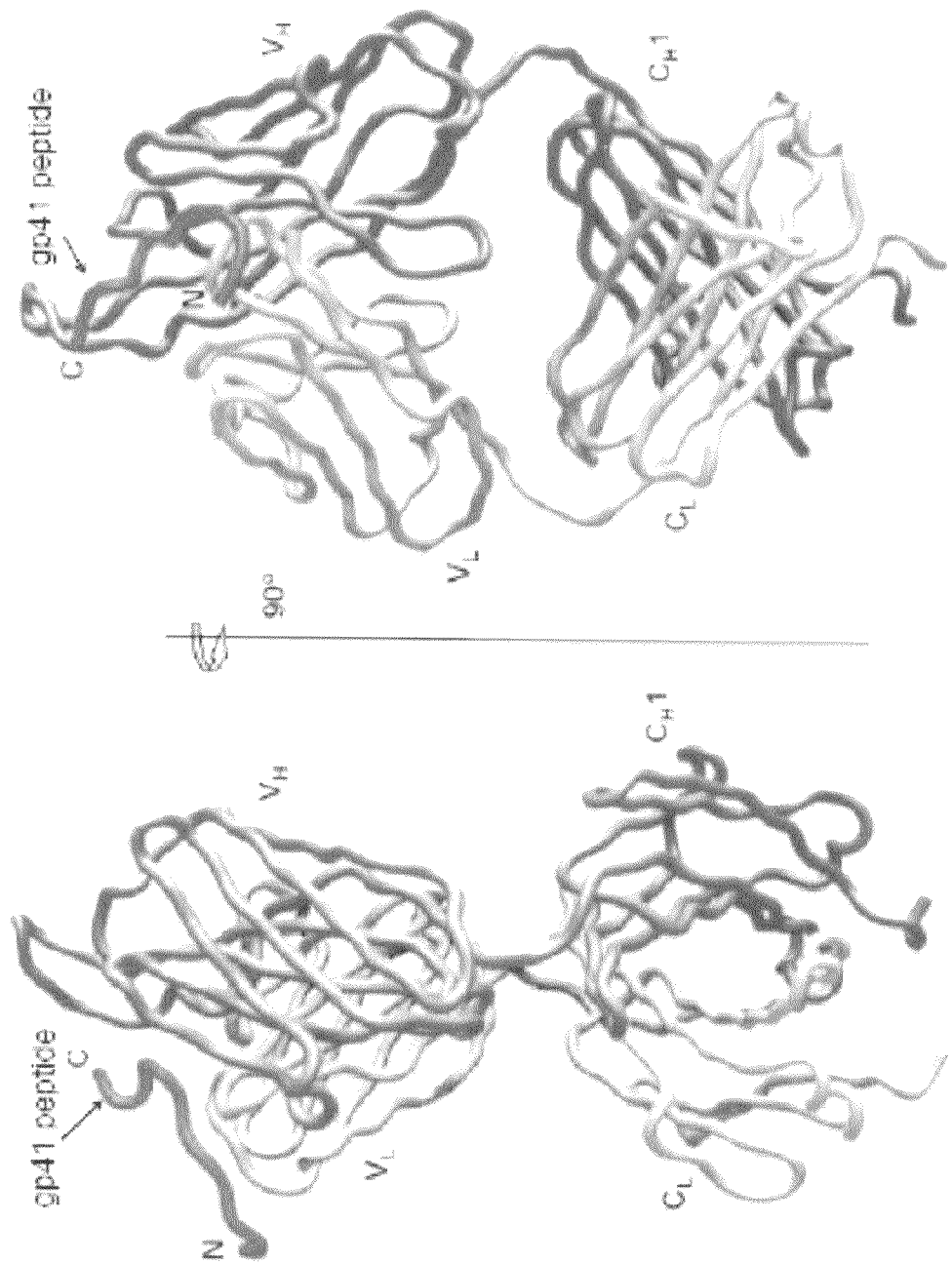

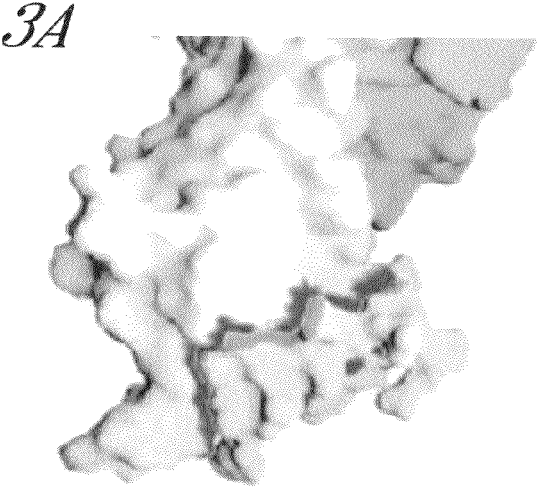
FIG. 3A
FIG. 3B
non-bound face
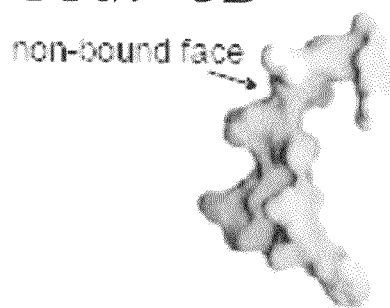
FIG. 3C
2F5 bound face (green)
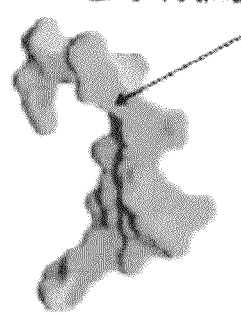
FIG. 3D
hydro-
phobic
face
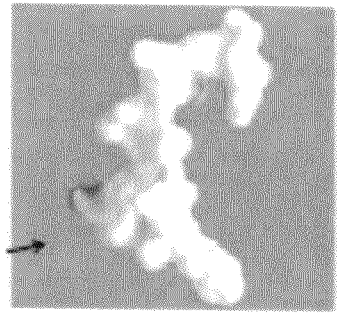
180°
FIG. 3E
charged face
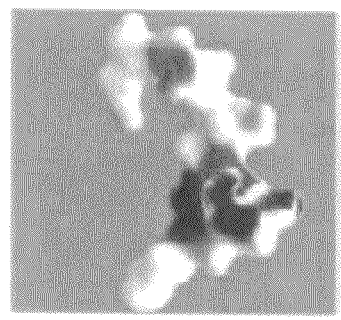

Viral Membrane

| | b12 | 2F5 | 4E10 | HA |
|---|---|---|---|---|
| JRFLgp145 | −/− | ++/++ | ++/+ | (−/−) |
| 2F5−4E10 | (−/−) | +/++ | +/++ | (−/−) |
| HA−2F5−4E10 | (−/−) | +/+ | ++/+ | −/− |
| 2F5−HA−4E10 | (−/−) | −/+ | +/+ | −/− |
| 2F5−4E10−H

Conformational stabilization disulfide-bond/
lactam-bridge

Surface occlusion

Occlude surface
with carbohydrate

Membrane context

VLPs or PLs membrane

Prime-boost gp120 &
gp41

Prime                                            Boost

Panel A
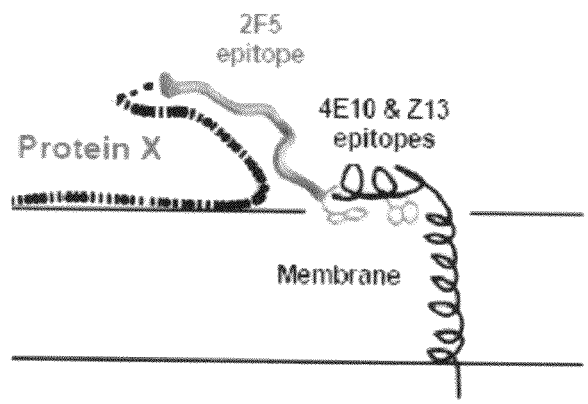
Panel B
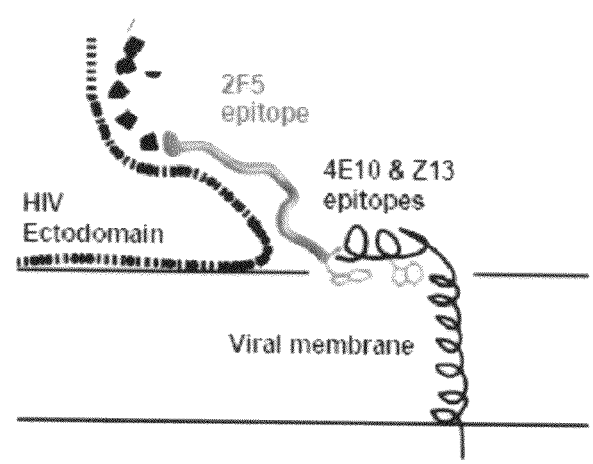
Panel C
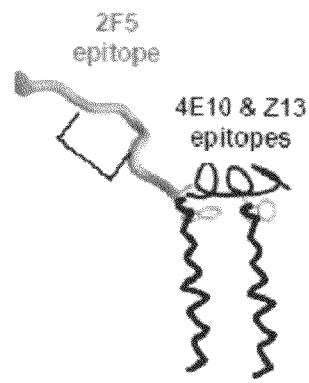
*FIG. 10*

FIG. 14

```
                          <-----------------------------------F  R  1  -  I  M  G  T----------------------------->
                          1                     5                    10                    15
input     IGHV2-5*10      AGG ATC ACG TTA AAG GAA TCG GGT CCT ...   CCG CTG GTG AAA CCC ACA CAG ACT
X69690    IGHV2-5*10      CA- --- --C --G --- --G --T --- ---      A-- --- --- --- --- --- --- --C
L21964    IGHV2-5*05      CA- --- --C --G --- --G --T --- ---      A-- --- --- --- --- --- --- --C
X62111    IGHV2-5*01      CA- --- --C --G --- --G --T --- ---      A-- --- --- --- --- --- --- --C
L21972    IGHV2-5*09      CA- G-- --C --G --- --G --T --- ---      A-- --- --- --- --- --- --- --C
L21968    IGHV2-5*07      CA- --- --C --G --- --G --T --- ---      A-- --- --- --- --- --- --- --C _____CDR1 - IMGT_____
                          20                    25                    30                    35
input     IGHV2-5*10      CTC ACG CTG ACC TGT TCC TTC TCT GGG TTC TCA CTG TCC GAT ACT TTT GGA GTG GGT
X69690    IGHV2-5*10      --- --- --- --- --- --C A-- --- --- --- --- --C AG- AC- AG- --- --- ---
L21964    IGHV2-5*05      --- --- --- --- --- --C A-- --- --- --- --- --C AG- AC- AG- --- --- ---
X62111    IGHV2-5*01      --- --- --- --- --- --C A-- --- --- --- --- --C AG- AC- AG- --- --- ---
L21972    IGHV2-5*09      --- --- --- --- --- --C A-- --- --- --- --- --C AG- AC- AG- --- --- ---
L21968    IGHV2-5*07      --- --- --- --- --- --C A-- --- --- --- --- --C AG- AC- AG- --- --- ---

_____F  R  2  -  I  M  G  T_____
                          40                    45                    50
input     IGHV2-5*10      ... ... ... GTG GGC TGG ATC CGT CAG CCC CCA GGA AAG GCC CTA GAG TGG CTT GCA
X69690    IGHV2-5*10      ... ... ... --- --- --- --- --- --- --- --- --- --- --- --G --- --- --- ---
L21964    IGHV2-5*05      ... ... ... --- --- --- --- --- --- --- --- --- --- --- --G --- --- --- ---
X62111    IGHV2-5*01      ... ... ... --- --- --- --- --- --- --- --- --- --- --- --G --- --- --- ---
L21972    IGHV2-5*09      ... ... ... --- --- --- --- --- --- --- --- --- --- --- --G --- --- --- ---
```

FIG. 15A

| | | | | | CDR2 - IMGT | | | | | | | | | | | |
|---|---|---|---|---|---|---|---|---|---|---|---|---|---|---|---|---|
| | | 55 | | | 60 | | | 65 | | | | CGC | TAC | AGC | CCA | TCG | CTG | AAC |
| input | | ATC | ATT | TAT | TCG | GAT | GAT | AAG | ... | ... | ... | | | | | 70 | | |
| X69690 | IGHV2-5*10 | C-- | --- | --- | -G- | --- | --- | --- | | | | --- | --- | --- | --- | --T | --- | --G |
| L21964 | IGHV2-5*05 | C-- | --- | --- | -G- | --- | --- | --- | | | | --- | G-- | --- | --- | --T | --- | --G |
| X62111 | IGHV2-5*01 | C-- | --- | --- | -G- | A-- | --- | --- | | | | --- | --- | --- | --- | --T | --- | --G |
| L21972 | IGHV2-5*09 | C-- | --- | --- | -G- | --- | --- | --- | | | | --- | G-- | --- | --- | --T | --- | --G |
| L21968 | IGHV2-5*07 | C-- | --- | --- | -G- | A-- | --- | --- | | | | --- | --- | --- | --- | --T | --- | --G |

| | | | | F | R | 3 | | | | - | I | M | G | T | | | 90 | |
|---|---|---|---|---|---|---|---|---|---|---|---|---|---|---|---|---|---|---|
| | | | 75 | | | | 80 | | | | | 85 | | | | | | |
| input | | ... | ACC | AGA | CTC | ACC | ATC | ACC | AAG | GAC | ACC | TCC | AAA | AAT | CAA | GTT | GTC | CTT | GTC |
| X69690 | IGHV2-5*10 | | -G- | --G | --- | --- | --- | --- | --- | --- | --- | --- | --- | --C | --- | --G | --G | --- | --- |
| L21964 | IGHV2-5*05 | | -G- | --G | --- | --- | --- | --- | --- | --- | --- | --- | --- | --C | --- | --G | --G | --- | --- |
| X62111 | IGHV2-5*01 | | -G- | --G | --- | --- | --- | --- | --- | --- | --- | --- | --- | --C | --- | --G | --G | --- | --- |
| L21972 | IGHV2-5*09 | | -G- | --G | --- | --- | --- | --- | --- | --- | --- | --- | --- | --C | --- | --G | --G | --- | --- |
| L21968 | IGHV2-5*07 | | -G- | --G | --- | --- | --- | --- | --- | --- | --- | --- | --- | --C | --- | --G | --G | --- | --- |

| | | | | | | 95 | | | | 100 | | | | | | | | |
|---|---|---|---|---|---|---|---|---|---|---|---|---|---|---|---|---|---|---|
| input | | ATG | ACT | AGG | GTG | AGT | CCT | GTG | GAC | ACA | GCC | ACG | TAT | TTC | TGT | | | | |
| X69690 | IGHV2-5*10 | --- | --C | -AC | A-- | GAC | --- | --- | --- | --- | --- | --A | --- | -A- | --- | | | | |
| L21964 | IGHV2-5*05 | --- | --C | -AC | A-- | GAC | --- | --- | --- | --- | --- | --A | --- | -A- | --- | | | | |
| X62111 | IGHV2-5*01 | --- | --C | -AC | A-- | GAC | --- | --- | --- | --- | --- | --A | --- | -A- | --- | | | | |
| L21972 | IGHV2-5*09 | --- | --C | -AC | A-- | GAC | --- | --- | --- | -G- | --- | --A | --- | -A- | --- | | | | |
| L21968 | IGHV2-5*07 | --- | --C | -AC | A-- | GAC | --- | --- | --- | --- | --- | --A | --- | -A- | --- | | | | |

HUMAN IMMUNODEFICIENCY VIRUS (HIV) IMMUNIZATION STRATEGIES EMPLOYING CONFORMATIONALLY-STABILIZED, SURFACE-OCCLUDED PEPTIDES COMPRISING A GP41 2F5 EPITOPE IN ASSOCIATION WITH LIPID

CROSS-REFERENCE TO RELATED APPLICATIONS

This application is a U.S. National Phase of International Application No. PCT/US2005/016633, filed May 13, 2005, designating the U.S. and published in English on Nov. 24, 2005 as WO 2005/111079, which claims a right of priority to U.S. Patent Application Ser. No. 60/570,883, filed May 14, 2004, which application is hereby incorporated by reference in its entirety.

STATEMENT OF GOVERNMENTAL INTEREST

This invention is funded by the National Institute of Allergy and Infectious Disease at the National Institutes of Health. The United States Government has certain rights to this invention.

FIELD OF THE INVENTION

This invention relates to novel peptide immunogens that generate an immune response in mammals against HIV gp41, to pharmaceutical composition that comprise such immunogens, and to methods of treating Immunodeficiency disease, especially HIV infection and AIDS, that employ such pharmaceutical compositions.

BACKGROUND OF THE INVENTION

The human immunodeficiency virus (HIV) is a pathogenic retrovirus (Varmus, H. (1988) "RETROVIRUSES," Science 240: 1427-1439; Cowley S. (2001) "THE BIOLOGY OF HIV INFECTION" Lepr Rev. 72(2):212-20). It is the causative agent of acquired immune deficiency syndrome (AIDS) and related disorders (Gallo, R. C. et al. (1983) "Isolation of human T-cell leukemia virus in acquired immune deficiency syndrome (AIDS)," Science 220(4599):865-7; Barre-Sinoussi, F. et al. "ISOLATION OF A T-LYMPHOTROPIC RETROVIRUS FROM A PATIENT AT RISK FOR ACQUIRED IMMUNE DEFICIENCY SYNDROME (AIDS)," (1983) Science 220:868-870; Gallo, R. et al. (1984) "FREQUENT DETECTION AND ISOLATION OF CYTOPATHIC RETROVIRUSES (HTLV-III) FROM PATIENTS WITH AIDS AND AT RISK FOR AIDS," Science 224:500-503; Teich, N. et al. (1984) "RNA TUMOR VIRUSES," Weiss, R. et al. (eds.) Cold Spring Harbor Press (NY) pp. 949-956). HIV acts to compromise the immune system of infected individuals by targeting and infecting the CD4$^+$ T lymphocytes that would otherwise be the major proponents of the recipient's cellular immune system response (Dalgleish, A. et al. (1984) "THE CD4 (T4) ANTIGEN IS AN ESSENTIAL COMPONENT OF THE RECEPTOR FOR THE AIDS RETROVIRUS," Nature 312: 767-768, Maddon et al. (1986) "THE T4 GENE ENCODES THE AIDS VIRUS RECEPTOR AND IS EXPRESSED IN THE IMMUNE SYSTEM AND THE BRAIN," Cell 47:333-348; McDougal, J. S. et al. (1986) "BINDING OF HTLV-III/LAV TO T4+ T CELLS BY A COMPLEX OF THE 110K VIRAL PROTEIN AND THE T4 MOLECULE," Science 231:382-385). HIV infection is pandemic and HIV-associated diseases represent a major world health problem.

HIV infection is believed to occur through the fusion of viral-cell and cell-cell membranes. This process is mediated by the gp41 and gp120 HIV env proteins and the cellular CD4 protein. Following binding of gp120 to CD4, a conformational change occurs in the gp120/gp41 complex. This change leads to the insertion of the gp41 protein into the target membrane and ultimately to membrane fusion.

SUMMARY OF THE INVENTION

In one aspect, the invention relates to an isolated peptide that comprises at least ten contiguous amino acids of the sequence EKNEQELLELDKWASLW (SEQ ID NO:1) and that binds to monoclonal antibody 2F5, wherein the isolated peptide is conformationally stabilized to provide a three dimensional structure that corresponds to that of the peptide EKNEQELLELDKWASLW (SEQ ID NO: 1) when complexed with the 2F5 antibody, wherein said isolated peptide comprises a face that does not bind to the 2F5 antibody.

In a further aspect, the invention relates to a method of generating an immune response against a gp41 antigen in a mammal comprising administering to the mammal an isolated peptide that comprises at least ten contiguous amino acids of the sequence EKNEQELLELDKWASLW (SEQ ID NO:1) and that binds to monoclonal antibody 2F5, wherein the isolated peptide is conformationally stabilized to provide a three dimensional structure that corresponds to that of the peptide EKNEQELLELDKWASLW (SEQ ID NO: 1) when complexed with the 2F5 antibody, wherein said isolated peptide comprises a face that does not bind to the 2F5 antibody of claim 2.

In a further aspect, the invention relates to a method of generating an immune response against a gp41 antigen in a mammal comprising administering to the mammal and expressible genetic construct comprising: (a) a polynucleotide encoding a heterologous leader sequence; (b) a polynucleotide encoding a heterologous hydrophobic polypeptide sequence; (c) a gp41 polynucleotide encoding at least ten contiguous amino acids of the MPR region of gp41; and (d) a polynucleotide encoding a heterologous transmembrane domain.

In a further aspect, the invention relates to an isolated crystal of the Fab' monoclonal antibody 2F5 complexed with a peptide having the amino acid sequence: EKNEQELLELDKWASLW (SEQ ID NO: 1) or a functional analog thereof.

BRIEF DESCRIPTION OF THE FIGURES

The patent or application file contains at least one drawing executed in color. Copies of this patent or patent application publication with color drawings will be provided by the Office upon request and payment of the necessary fee.

FIG. 1 shows the overall structure of the 2F5-Fab-gp41$_{654-670}$ 17-mer complex. Panel A shows C$_\alpha$ traces of the 2F5 Fab heavy chain and light chain and of the gp41 peptide from residue Glu$_{657}$ to Trp$_{670}$; Panel B shows a 90° view of the same traces.

FIG. 3 is a schematic illustration of the 2F5 binding surface on gp41. Panel A shows a molecular surface representation of 2F5 complexed to gp41. The orientation shown is similar to that in FIG. 4. Colored in magenta is the surface on 2F5 that is buried by the interaction with gp41, and colored in green is the surface on gp41 that is buried by the interaction with 2F5. Panels B and C show close-ups of the peptide. The gp41 peptide molecular surface from Panel A is oriented so that $Trp_{670}$ is at the bottom of the panel and the N terminus of the peptide is at the top; 180° views are shown. Roughly 40% of the surface of the gp41 peptide is buried by 2F5, while the remaining surface remains hidden. Panels D and E show the electrostatic potential of the peptide. When the molecular surface of the peptide is colored by electrostatic potential, it becomes apparent that the surface that is bound by 2F5 is charged (Panel E), while the surface that is hidden from 2F5 is hydrophobic (Panel D). The electrostatic potential shown is colored at the same potential contour as in FIG. 2, Panel A, with red for electronegative, blue for electropositive, and white for apolar (Nicholls et al., 1991, Protein folding and association: insights from the interfacial and thermodynamic properties of hydrocarbons, *Proteins* 11:281-296).

Figure 4A:
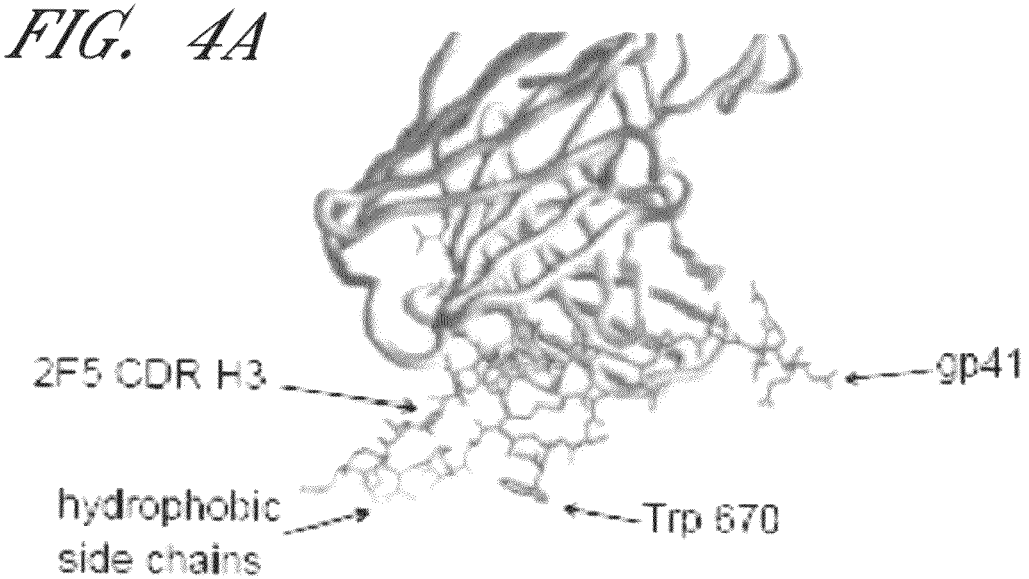
Figure 4B:
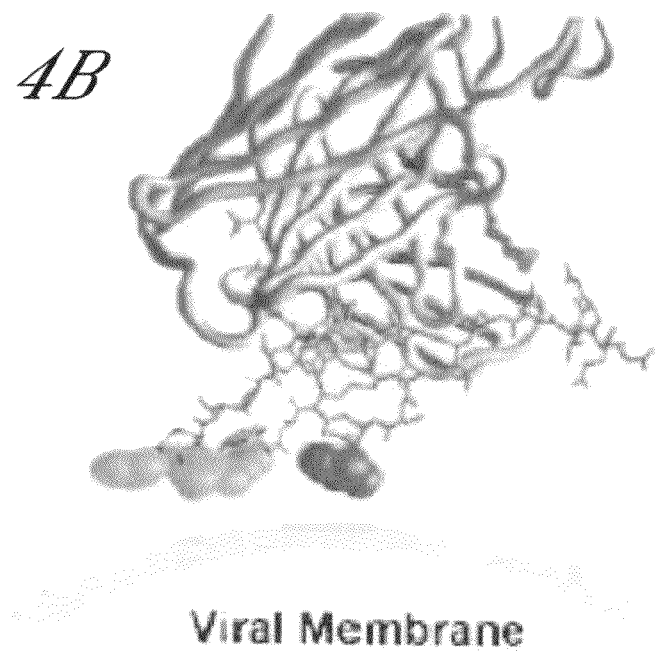

FIG. 4 shows the CDR H3 loop of 2F5. 2F5, with the heavy chain in blue and the light chain in gray. Atomic bond representations are shown for the 2F5 CDR H3 loop, and the gp41 peptide. In Panel A side chains of hydrophobic residues at the apex of the CDR H3 loop ($Leu_{H100a}$, $Phe_{H100b}$, $Val_{H100d}$, and $Ile_{H100f}$) are indicated. These residues define a hydrophobic surface which if extended as a plane intersects the indole ring of $Trp_{670}$. In Panel B, the coplanarity of these hydrophobic side chains is evident when the atoms of the side chains are shown in a space-filling representation. The hydrophobic plane defined by these apical CDR H3 residues may be an adaptation that allows 2F5 to bind at or in close proximity to the viral membrane.

Figure 5:
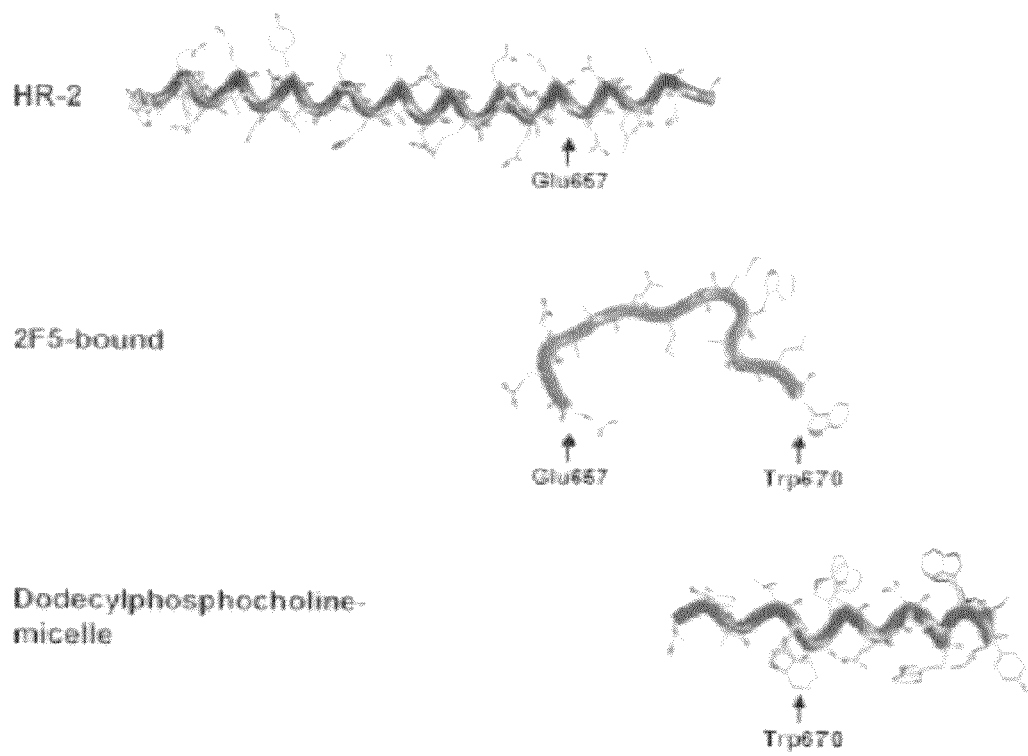

FIG. 5 shows a comparison of the 2F5-bound conformation of gp41 (SEQ ID NO: 27) with other gp41 conformations. Shown are the structure of the HR2 helix observed in the structure of the postfusion six-helix bundle (Weissenhorn et al., 1997, Atomic structure of the ectodomain from HIV-1 gp41, *Nature* 387:426-430), the structure of 2F5-bound gp41 presented here, and the NMR structure of the membrane-proximal region of gp41 in the context of dodecylphosphocholine micelles (Schibli et al., 2001, The membrane-proximal tryptophan-rich region of the HIV glycoprotein, gp41, forms a well-defined helix in dodecylphosphocholine micelles, *Biochemistry* 40:9570-9578). The structures are aligned not according to biological context, but relative to the $C_\alpha$ positions of residues $Glu_{657}$ and $Trp_{670}$. The helices of both the six-helix bundle and the downstream micellar structure would have to partially unravel for gp41 to adopt the 2F5-bound conformation. The sequences of the three structures (SEQ ID NO: 28; 29 and 30) are aligned at the top, and the sequences of disordered residues are shown in light gray.

Figure 6:
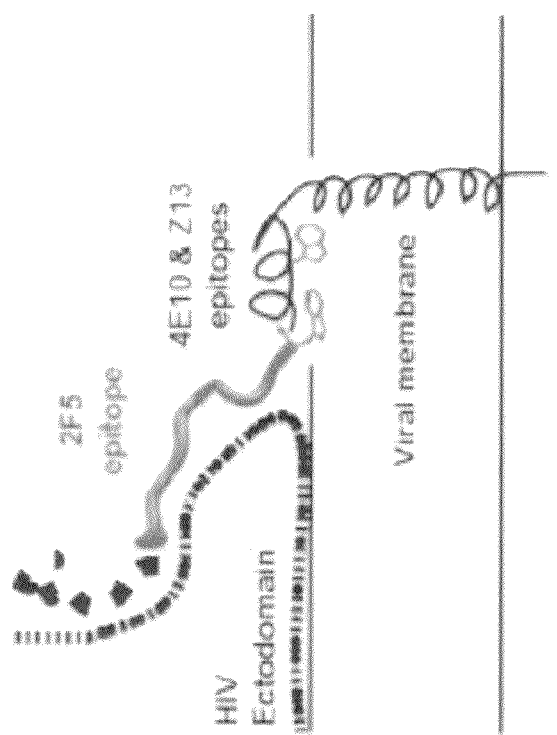

FIG. 6 shows the transmembrane-proximal region of gp41. This schematic shows the 2F5 epitope with its hidden face occluded by the HIV ectodomain. The conformation of the N-terminal adjoining region is not known. The C-terminal region adjoining the 4E10 and Z13 epitopes is shown as a helix lying parallel to the viral membrane, with $Trp_{670}$ and $Trp_{678}$ embedded in the lipid bilayer. Although the 4E10-Z13 epitope is shown for visual clarity as extending away from the rest of the HIV ectodomain, the angle it makes with the 2F5 epitope is unknown, and it is likely to be partially occluded in the viral spike.

Figure 7A:
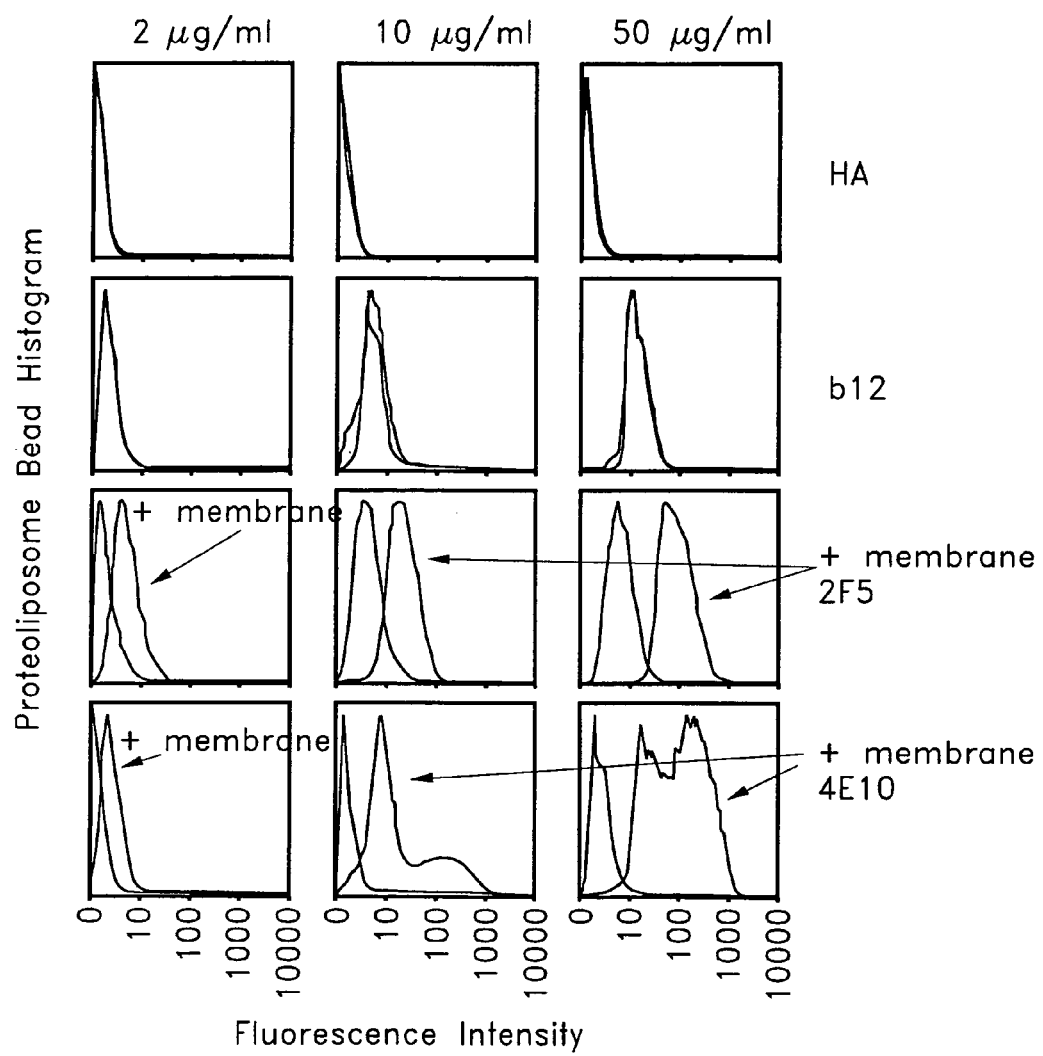

FIG. 7 shows a biochemical analysis of the effect of lipid membrane and hydrophobic context on 2F5 and 4E10 binding. PLs composed of paramagnetic beads conjugated to the 1D4 antibody are used to capture different envelope constructs through C-terminal C9 tags, which are recognized by 1D4. Each of the envelope constructs retained the native JRFL transmembrane domain (TM), so that envelope-TM-captured PLs incubated with lipids simulated the native TM in a lipid bilayer. Alternatively PLs could be washed extensively with detergent to remove bound lipid and expose the naked TM. In this manner, PLs with and without lipid membrane could be prepared. Panel A shows a flow cytometry analysis of b12, 2F5, and 4E10 binding to PLs with and without lipid membrane. Fluorescently labeled antibodies at 2 μg/ml (left panels), 10 μg/ml (middle panels), and 50 μg/ml (right panels) are incubated with JRFL gp145-captured PLs. Histograms (normalized for 100,000 events) of the flow cytometry-sorted PL fluorescence intensity are shown for PLs with membrane (red) and without membrane (blue). Panel B shows the effect of context on the binding of 2F5 and 4E10. Five different PLs are analyzed, each with the 2F5 and 4E10 epitopes placed in a different context. A schematic of each context is shown, with gp120 referring to the cleavage-minus N-terminal gp120 attached to gp41; 2F5, 4E10, and HA referring to the respective epitopes of 2F5, 4E10, and the antihemagglutinin antibody sc-7392; and TM and C9 referring to the JRFL transmembrane region and 1D4-recognized tag, respectively. Each PL is tested for binding to fluorescently labeled antibodies b12, 2F5, 4E10, and HA, either in the presence of membrane or after extensive detergent washing to remove membrane. The relative fluorescence with and without membrane is tested over an antibody concentration range of 2 to 200 μg/ml. The results of two independent experiments are shown (presented as result for experiment 1/result for experiment 2). ++, 10- to 50-fold-greater fluorescence in the presence of membrane; +, 2- to 10-fold-greater fluorescence; –, 0.5- to 2.0-fold-greater fluorescence. Parentheses indicate that the particular antibody epitope is not present on the construct, and asterisks indicate that the overall level of antibody binding is low, both with and without membrane. As can be seen, not only the presence of lipid membrane but also the surrounding sequence influences optimal 2F5 and 4E10 epitope recognition.

Figure 8A:
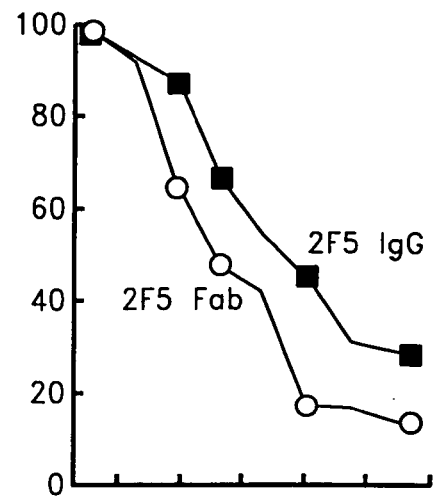
Figure 8B:
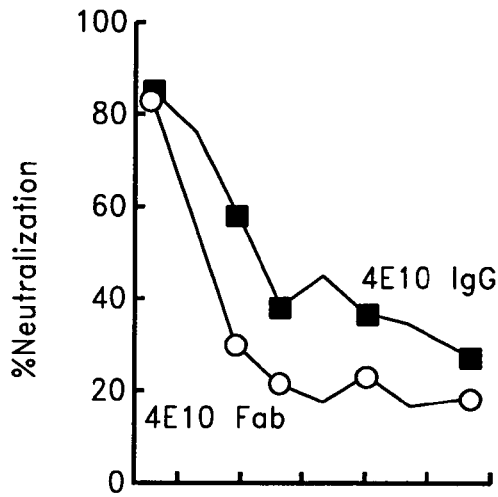
Figure 8C:
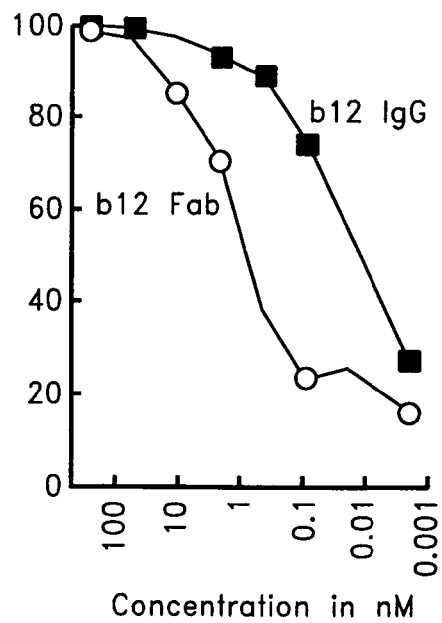
Figure 9A:
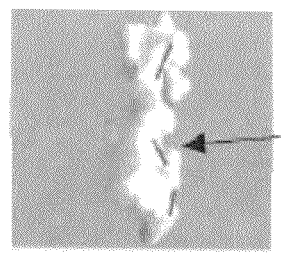
Figure 9B:
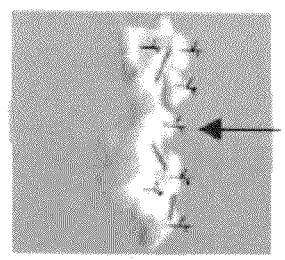
Figure 9C:
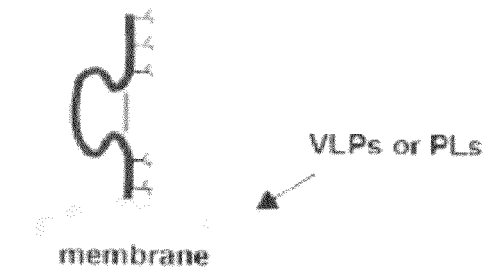
Figure 9D:

FIG. 8 shows the neutralization of HIV-1 isolate JRFL by IgG versus Fab. In order to assess the existence of steric hindrance of access of IgG molecules to membrane-proximal region epitopes, neutralization capacities of IgGs (squares) versus Fabs (circles) are compared for 2F5 (Panel A), 4E10 (Panel B), and b12 (Panel C) as a control. The concentrations of the IgGs and Fabs ranged from 0.002 to 300 nM. Neutralization data are obtained with CD4 T cells as target cells and flow cytometry of anti-p24 antibody-stained cells to assess the number of infected cells after a single round of virus infection. The percentage of neutralization is calculated as the reduction in the number of infected cells compared to the number of infected cells in wells incubated with mock antibody. Similar results are obtained for HIV-1 strain SF162.

FIG. 9 illustrates a vaccine immunization strategy. A four-part strategy to elicit 2F5-like antibodies is shown. Panel A shows the conformational stabilization of the 2F5-bound extended conformation of gp41. The molecular surface of a potential immunogen is shown in a color scheme similar to that in FIG. 3, Panels B and C, with the surface bound by 2F5 colored in green and the surface hidden from 2F5 colored in white. Disulfide bonds or lactam bridges that stabilize conformation are shown in magenta. Panel B shows the occlusion of the hidden face of gp41. Carbohydrate (black) is shown occluding the hidden hydrophobic surface of gp41 from humoral immune recognition. Due to the size of the epitope, N-linked glycans may be too large to use here, but smaller O-linked glycans may allow more precise masking. Panel C shows a membrane context for immunogen presentation. To elicit antibodies that are able to accommodate an epitope that is proximal to membrane, one could immunize with a conformationally stabilized, surface-occluded immunogen in the context of membrane, either on virus-like particles (VLPs) or on PLs. Panel D shows a prime-boost strategy for immunization. Various prime-boost strategies could be employed to select only those antibodies that are able to overcome accessibility barriers to the membrane-proximal region. Shown here is one example, with the prime consisting of a conformationally stabilized, surface-occluded immunogen presented in the context of membrane. A boost with the complete Env ectodomain should select antibodies that can bind to the native viral spike.

FIG. 10 shows three examples of immunogen platforms. Panels A and B show schematic illustrations of the results of immunizations with nucleic acid molecules (i.e. genetic immunizations) that encode the 2F5 epitope in association with the 4E10 & Z13 epitopes, a transmembrane domain, and a heterologous protein X (Panel A) or gp41 ectodomain sequence (Panel B) that have been designed for desired presentation of the 2F5 epitope. Panel C is a schematic representation of a 2F5 peptide immunogen, wherein the peptide has been designed for the desired presentation of the 2F5 epitope.

FIG. 11 shows a representative set of initial gp41 constructs. A set of gp41 constructs were rationally designed based on the 28mer construct. Hydrophobic CD4-TM or fusion peptide residues were added to the 28mer potentially enhance lipid bilayer association. The C34 and ½ C34 was added to as "spacers".

FIG. 12 shows FACS analysis of 2F5 Ab binding.

FIG. 13 shows FACS analysis of 4E10 Ab binding.

FIG. 14 was intentionally left blank.

FIG. 15 shows the alignment of input sequence (SEQ ID NO: 21) with polynucleotides encoding immunoglobulins X69690-IGHV2-5*10 (SEQ ID NO: 22); L21964-IGVH2-5*05 (SEQ ID NO: 23); X62111-IGVH2-5*01 (SEQ ID NO: 24); L21972-IGVH2-5*09 (SEQ ID NO: 25); and L21968-IGVH2-5*10 (SEQ ID NO: 26).

DESCRIPTION OF THE PREFERRED EMBODIMENTS

As the HIV pandemic continues to infect millions of people each year, the need for an effective vaccine increases. The development of such a vaccine has been stymied due to the difficulty in developing an immunogen capable of eliciting broadly neutralizing antibodies. In order to develop such an immunogen, a crystallographic investigation of the broadly neutralizing, anti-HIV-1 antibody, 2F5 is undertaken. Antibody 2F5 is discussed by Pai, E., et al. (2000) ("Fab'-Epitope Complex From The HIV-1 Cross-Neutralizing Monoclonal Antibody 2F5," PCT Publication No. WO-00/61618), and by Barbato, G., et al. (2003) ("Structural Analysis Of The Epitope Of The Anti-HIV Antibody 2F5 Sheds Light Into Its Mechanism Of Neutralization And HIV Fusion," J. Molec. Biol 330:1101-1115), (see, also, Vaccine Research Centerpost-doctoral fellow seminar, Jun. 3, 2003, and Vaccine Research Center retreat seminar, Nov., 13, 2003), all of which references are herein incorporated by reference.

By solving the crystal structure of 2F5 in complex with a 17-mer gp41 peptide, insight is gained into the mechanism of 2F5-mediated neutralization of HIV, and thereby into how to design vaccine immunogens to elicit similarly broadly neutralizing antibodies against HIV. The crystal structure has also provided insight into the design of anti-HIV-1 therapeutics. Such structural analysis has led to a complete structural model of the membrane-proximal region of HIV gp41, which is a region of HIV that is vulnerable not only to 2F5-mediated neutralization, but also to 4E10- and Z13-mediated neutralization—two additional broadly neutralizing anti-HIV antibodies. It has also led to a four-part vaccine strategy for eliciting 2F5-like broadly neutralizing anti-HIV antibodies. This vaccine strategy includes conformational stabilization of gp41, proper surface occlusion of gp41, membrane-context presentation of gp41, and a prime-boost strategy to selectively drive the in vivo production of antibodies that can bind to the native envelope spike. Certain concepts of this vaccine strategy can be adapted for use against other regions of HIV, or against other viruses, and can be used in conjunction with structure-based therapeutics as proposed herein This invention relates to novel immunogens that generate an immune response in mammals against HIV gp41, to pharmaceutical compositions that comprise such immunogens, and to methods of treating Immunodeficiency disease, especially HIV infection and AIDS, that employ such pharmaceutical compositions.

Isolated Peptide Immunogens

In one embodiment the invention relates to an isolated peptide that binds to monoclonal antibody 2F5, or a fragment thereof, and that comprises at least ten contiguous amino acids, preferably at least 12 contiguous amino acids, more preferably at least 14 contiguous amino acids, and most preferably at least 16 contiguous amino acids of the sequence EKNEQELLELDKWASLW (SEQ ID NO:1), wherein the isolated peptide is conformationally stabilized to provide a three dimensional structure that corresponds to that of the peptide EKNEQELLELDKWASLW (SEQ ID NO: 1) when complexed with the 2F5 antibody, wherein said isolated peptide comprises a face that does not bind to the 2F5 antibody.

In the present invention, "isolated" refers to material removed from its original environment (e.g., the natural environment if it is naturally occurring), and thus is altered "by the hand of man" from its natural state.

An isolated peptide may comprise a portion of a larger molecular complex. For example, an isolated peptide may comprise a portion of a larger peptide, protein, or polypeptide. The isolated peptide may linked to other functional moieties such as, for example, T-cell epitopes. Isolated peptides may also be in a complex with other components such as adjuvants. In a preferred embodiment of the invention, isolated peptides are associated with proteoliposomes. Specific examples include the following: (1) Link KLH onto the C-terminus. (2) Link N/C termini to a heterologous T-helper motif (e.g., PADRE). (3) Link N/C termini with a monophospholipid-A adjuvant which would be recognized by CD1-like MHC.

In a preferred embodiment of the invention isolated peptides are presented in a membrane context. For example, in one embodiment, solid-phase proteoliposomes (PLs) or virus-like particles may be employed to present conformationally stabilized and surface occluded immunogens. In a preferred embodiment, isolated peptides of the invention are associated with a transmembrane component. As used herein, a "transmembrane component" is any molecule that is anchored in the membrane and serves the purpose of localizing the isolated peptides of the invention in juxtaposition to the membrane. Preferably, the isolated peptide is juxtaposed to the membrane so that the face of the isolated peptide that does not bind to the 2F5 antibody is located adjacent to the membrane.

In one embodiment of the invention dimers, trimers or oligomers, or high density displays of the isolated peptides are employed. For example, linkage of a His-tagged immunogen to a nickel bead could form a high-density display of the antigen.

In a preferred embodiment of the invention, the face of the isolated peptide that does not bind to the 2F5 antibody is occluded. Occlusion may be accomplished, for example, using the following methods: (A) Lipid. Occlusion of the non-2F5-bound face of gp41 could be achieved by attaching lipid to this face, and then immunizing in the context of membrane. (B) O-linked glycans. These glycans are relatively small and so allow for more precise occlusion of the non-2F5-bound face. Ideally, O-linked glycans could be attached to non-buried residues of the 2F5-epitope—Leu660 (which would have to be mutated to a serine or threonine for O-linked glycosylation) or Ser668 which could stay as it is. Other residues of the epitope could be mutated and then O-glycosylated in order to more fully occlude the non-2F5-bound face. (C). N-linked glycans. Though N-linked glycans are much larger than O-linked ones, their size could have the benefit of making occlusion of the non-2F5-bound face of the membrane-proximal region more complete with fewer attachments. (D) Attaching reactive groups to the non-2F5-bound face and then reacting the immunogen with a complementary reactive surface would leave non-2F5-bound face occluded while exposing the 2F5-bound face. Such a scenario could be performed while in complex with 2F5 (which would be eluted off) in order to ensure proper conformation. (E) Due to the natural hydrophobicity of the non-2F5-bound face of the membrane proximal region, placement on a complementary hydrophobic surface (e.g., graphite) could be sufficient for occluding the non-2F5-bound face.

In a preferred embodiment of the invention, isolated peptides further comprise the 4E10/Z13 epitope i.e. NWFNIT (SEQ ID NO: 2).

Isolated peptides of the invention may be conformationally stabilized in any of a number of ways, including for, example, the use of disulfide bonds or lactam bridges. Considerations for conformational stabilization include the following: (A) For constraining Trp670 and Trp678 in the membrane, these residues can be replaced with large hydrophobic groups/lipids (e.g., inositol). This would ensure that the correct face of the helix (that containing Trp670 and Trp678) lies along the membrane, while the opposite face is exposed. (B) The transmembrane domain can be replaced with an attached lipid; this would be advantageous because it would make the immunogen smaller. (C) Disulfide bonds or lactam bridges might be employed to stabilize the b-turns that are present in the 2F5-bound conformation of gp41 or to stabilize the downstream helix that lies along the face of the membrane. (D) Reactive groups can be attached to the non-2F5-bound hydrophobic face of the membrane proximal region, and then, while in complex with 2F5, bind this immunogen to a surface that would react with the attached reactive groups. After elution of 2F5, one could be left with an immunogen that is in the correct 2F5-bound conformation.

The polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

The polypeptides and proteins of the present invention can be composed of amino acids joined to each other by peptide bonds or modified peptide bonds, i.e., peptide isoteres, and may contain amino acids other than the 20 gene-encoded amino acids. The polypeptides may be modified by either natural processes, such as posttranslational processing, or by chemical modification techniques. Both post-translational modifications and chemical modification techniques are well described in the art. Modifications can occur anywhere in a polypeptide, including the peptide backbone, the amino acid side-chains and the amino or carboxyl termini. The same type of modification may be present in the same or varying degrees at several sites in a given polypeptide, and a given polypeptide may contain many types of modifications. Polypeptides may be branched, for example, as a result of ubiquitination, and they may be cyclic, with or without branching. Cyclic, branched, and branched cyclic polypeptides may result from posttranslational natural processes or may be made by synthetic methods.

Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, *Proteins—Structure and Molecular Properties,* 2nd Ed., T. E. Creighton, W. H. Freeman and Company, New York (1993); *Posttranslational Covalent Modification of Proteins,* B. C. Johnson, Ed., Academic Press, New York, pgs. 1-12 (1983); Seifter et al., 1990, *Meth. Enzymol.* 182:626-646; Rattan et al., 1992, *Ann. NY Acad. Sci.* 663:48-62).

The polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

The invention additionally concerns a method of generating an immune response against a gp41 antigen in a mammal by administering to the mammal isolated peptides of the invention.

Nucleotide Immunogens

In one embodiment, the invention relates to nucleotide or genetic immunogens that encode at least a portion of the membrane proximal region of a gp41 envelope protein for expression in a membrane context that facilitates presentation of the 2F5 epitope region. Nucleotide immunogens are expressible in human cells, and the design of nucleotide immunogens that are expressible (i.e. the selection of vectors, promoters and other regulatory components for nucleotide expression) is within the skill of one in the art. Nucleotide immunogens may comprise either DNA or RNA.

In one embodiment, nucleotide immunogens encode an "MPR epitope". An "MPR epitope", as used herein, refers to a polypeptide that is at least 22 amino acids, preferably at least 24 amino acids, more preferably at least 26 amino acids, and most preferably at least 28 amino acids in length that is at least 90%, preferably 95%, more preferably 98%, and most preferably 100% homologous to a portion of the extracellular membrane adjacent 28 amino acids of an HIV-1 gp41 protein.

In one embodiment the invention comprises a polynucleotide construct that comprises the following components in 5' to 3' order:
a polynucleotide encoding a heterologous leader sequence;
a polynucleotide encoding a heterologous hydrophobic polypeptide sequence
a gp41 polynucleotide encoding at least ten, preferably at least 15, preferably at least 20 contiguous amino acids of the MPR region of gp41; and
a polynucleotide encoding a heterologous transmembrane domain.

Heterologous, as used herein, refers to components that are heterologous to the gp41 protein; components may or may not be heterologous to each other.

In one embodiment the invention comprises a human cell expressible polynucleotide construct that comprises the following components in 5' to 3' order:
a polynucleotide encoding a heterologous leader sequence;
a polynucleotide encoding a heterologous hydrophobic polypeptide sequence
a gp41 polynucleotide encoding an MPR epitope; and
a polynucleotide encoding a heterologous transmembrane domain.

In one embodiment, the invention comprises a human cell expressible polynucleotide construct comprising a polynucleotide that encodes a transmembrane framework protein comprising an MPR epitope in close proximity to the transmembrane domain.

The MPR epitope is preferably within 10, more preferably within 5, and most preferably within 3 amino acids of the transmembrane domain.

In a preferred embodiment, the gp41 polynucleotide encodes a polypeptide comprising the following sequence: NEQELLELDKWASLWNWFNITNWLWYIK (SEQ ID NO: 20).

Strategies for optimizing presentation of the MPR region are presented in Examples 2, 4 and 5 herein.

In one embodiment, the invention comprises a human cell expressible polynucleotide construct comprising a polynucleotide that encodes a transmembrane framework protein comprising an inserted MPR epitope located 5-prime of, and in close proximity, to the transmembrane domain. A "transmembrane framework protein" refers a protein that comprises a transmembrane domain that anchors the protein in the membrane protein. Transmembrane framework proteins may be derived from naturally occurring proteins or artificially designed.

Preferred transmembrane framework proteins for use in conjunction with the invention include the following: potassium channel protein, secYE&beta protein conducting channel proteins, photosynthetic reaction center, cytochrome bc1 complex (1QCR) protein, bacterial rhodopsin protein, beta-barrel membrane proteins.

Prime-Boost Strategies.

Elicitation of 2F5-like antibodies with the immunogens presented above could be enhanced with prime-boost strategies. For example, priming with a conformationally stabilized, surface occluded, membrane-anchored immunogen, may elicit high titers of antibodies, only a small portion of which recognize virus. A boost, on the other hand, composed of the complete wild type envelope ectodomain and presented in a membrane-anchored context, should then selectively drive the in vivo production of antibodies capable of binding wild-type virus. Conversely, one could also prime with the complete envelope ectodomain, and then boost with the smaller, more accessible immunogen. Listed below are four example candidates that may be employed in a prime/boost strategy: (1) Prime or boost with gp160 PLs. (2) Prime or boost with Adeno presented HIV-1 envelope glycoproteins. (3) Prime or boost with HIV-2/SIV envelope glycoproteins modified to posses the 2F5 and 4E10 epitopes. (4) Prime or boost with variant HIV-1 envelopes.

2F5 Single Chain FV as a Therapeutic Agent

The crystal structure shows that the N-terminus of the 2F5 light chain interacts with the gp41 epitope. Therefore, any effective single chain FV would preferably have the light chain at the N-terminus and the heavy chain at the C-terminus. Use of the 2F5 scFV may be valid as a therapeutic, or could have wide range use in numerous experimental settings for the further elucidation of the mechanism 2F5-mediated neutralization of HIV-1.

Mutagenesis of the 2F5 single chain FV in order to make it more potently neutralizing. Mutations would aim to either increase 2F5's affinity for its epitope, or would aim to increase 2F5's affinity for membrane by making certain residues more hydrophobic. Examples of mutations, either alone or in combination, of the 2F5 CDR H3 in order to increase epitope affinity include the following: 1) T99 mutated to a Phe. 2) A100g mutated to an Ile. 3) T99 to Phe and A100g to Ile. Mutations: either alone or in combination, of the 2F5 CDR H3 in order to increase membrane affinity include the following: 1) L100aW; 2) V100dF; 3) I100fW. Mutagenesis presented above could also be performed in the context of the 2F5 Fab or IgG.

The present invention also pertains to the use of a computer system to provide a representation of the binding of peptides and synthetic peptides to antibodies that recognize gp41 epitopes. As used herein, the term "computer system" encompasses a data input means, a data storage means, a data retrieval means, and a data processing means. Most preferably, the computer system will additionally contain one or more output devices, such as a monitor, printer, etc. In a preferred embodiment, the input means of the computer system will have the capacity to manipulate the representation, such as by focusing, zooming, positioning, rotating, shrinking, expanding, color-coding, etc., features of interest identified either by the computer system or by the user.

As used herein, the term "representation" as applied to three-dimensional molecular structure is intended to encompass pictorial, digital, as well as analog representations. Examples of pictorial representations include printed or video imaged atoms, molecules or supra-atomic representations.

The invention further concerns a computer system comprising data and a data processor, wherein the system forms a representation of the three-dimensional structure of the peptide EKNEQELLELDKISLW (SEQ ID NO:1), wherein said computer system optionally permits users to model representations of peptides and synthetic peptides for those having similar three-dimensional structures.

The invention further concerns a computer system comprising data and a data processor, wherein the system forms a representation of the three-dimensional structure of the binding site of the Fab' monoclonal antibody 2F5 that binds to the peptide EKNEQELLELDKISLW (SEQ ID NO:1), wherein said computer system optionally permits users to model representations of peptides and synthetic peptides for those having the ability to bind to such binding site.

In one aspect, the invention concerns an isolated crystal of the Fab' monoclonal antibody 2F5 complexed with a peptide having the amino acid sequence: EKNEQELLELDKISLW (SEQ ID NO:1) or a functional analog thereof.

Example 1

Structure and Mechanistic Analysis of the Anti-Human Immunodeficiency Virus Type 1 Antibody 2F5 in Complex with Its gp41 Epitope 2F5 IgG and Fab Production.

Human monoclonal antibody 2F5 is produced by recombinant expression in Chinese hamster ovary cells (Kunert et al., 2000, Stable recombinant expression of the anti HIV-1 monoclonal antibody 2F5 after IgG3/IgG1 subclass switch in CHO cells, *Biotechnol. Bioeng.* 67:97-103). The 2F5 antigen-binding fragment (Fab) is prepared by reducing 2F5 immunoglobulin G (IgG) (13 mg/ml) in 100 mM dithiothreitol (1 h, 37° C.), alkylating in 2 mM iodoacetamide (48 h, 4° C.), and then cleaving with endoproteinase Lys-C (0.01 μg/μl; Roche Applied Sciences) in 25 mM Tris Cl and 1 mM EDTA (pH 8.5) for 4 h at 37° C. The cleavage reaction is stopped with 1 mM TLCK (Na-p-tosyl-L-lysine chloromethyl ketone) and 0.4 mM leupeptin, and the cleavage products are passed over a protein A-Sepharose column (Sigma). Flow-through fractions are collected and subjected to cation-exchange chromatography (Mono S HR 5/5; Pharmacia-Amersham Biosciences) with a gradient ranging from 0 to 0.5 M NaCl in 50 mM Na acetate, pH 5.0. Peak fractions are combined and further purified by size exclusion chromatography (Superdex 200 HiLoad 26/60; Pharmacia-Amersham Biosciences) in gel filtration buffer (350 mM NaCl, 2.5 mM Tris-$SO_4$ [pH 7.1], 0.02% $NaN_3$).

2F5 Fab-gp41 Peptide Complex Formation.

The peptides $gp41_{662-668}$ (ELDKIS) (SEQ ID NO: 3), $gp41_{659-671}$ (ELLELDKISLWN) (SEQ ID NO: 4), and $P41_{656-674}$ (NEQELLELDKISLWNWFD) (SEQ ID NO: 5) and N-terminally acetylated and C-terminally amidated peptides $gp41_{661-669}$ (ac-LELDKISL-n) (SEQ ID NO: 6), $gp41_{660-670}$ (ac-LLELDKISLW-n) (SEQ ID NO: 7), and $gp41_{654-670}$ (ac-EKNEQELLELDKISLW-n) (SEQ ID NO: 1) are obtained through the National Institute of Allergy and Infectious Diseases (NIAID) peptide facility (J. Lukszo, Princeton Biomolecules, and American Peptide). Each lyophilized peptide is resuspended in 30% acetonitrile, combined with purified 2F5 Fab to a molar ratio of 3:1, placed in 0.5× gel filtration buffer (gel filtration buffer diluted 50% with water), and concentrated with a Centricon-10 instrument (Amicon) to between 5 and 10 mg/ml.

2F5 Fab-gp41 Peptide Complex Crystallization, Data Collection, Structure Determination, and Refinement.

All crystals are grown by hanging-drop vapor diffusion. Crystallization droplets are set up with 0.5 μl of protein (in 0.5× gel filtration buffer) and 0.35 μl of reservoir solution. Crystals of 2F5 complexed with 13-mer are grown with a reservoir solution of Hampton Crystal Screen reagent 18, composed of 0.2 M Mg acetate, 0.1 M Na cacodylate (pH 6.5), and 20% polyethylene glycol 8000 (PEG 8000). Crystals of 2F5 Fab complexed with 7-mer, 1'-mer, or 17-mer are grown with a reservoir solution composed primarily of Hampton Crystal Screen reagent 40. Microseeding (Stura and Wilson, 1991, Applications of the streak seeding technique in protein crystallization, *J. Crystal Growth* 110:270-282) and slight alterations in the concentration of the reservoir salt enhanced crystallization and increased reproducibility. For example, with the 2F5 Fab-17-mer complex, the reservoir solution is composed of 20% PEG 4000, 20% isopropanol, and 125 mM Na citrate (pH 5.6). After crystallization droplets are set up, additional NaCl is added to the reservoir to bring the final reservoir NaCl concentration to 100 mM, and crystals are obtained by heterologous cross-seeding with crystals of the 2F5-11-mer complex.

Before data are collected at 100 K, crystals are placed for a few minutes in a stabilizing cryoprotectant solution composed of the reservoir solution supplemented with PEG 4000 and ethylene glycol to final concentrations of 30% each. Flash cooling is aided by Paratone-N (Kwong and Yee, 1999, Use of cryoprotectants in combination with immiscible oils for flash cooling macromolecular crystals, *J. Appl. Crystallogr.* 32:102-105). X-ray data are collected with 1.000-Å radiation at the Advanced Photon Source, SER-CAT beamline 22, Argonne National Laboratory. Data are processed with HKL2000 (Otwinowski and Minor, 1997, Processing of X-ray diffraction data collected in oscillation mode, *Methods Enzymol.* 276:307-326).

The structure of the 2F5-$gp41_{662-668}$ 7-mer complex is solved by using molecular replacement with the program AmoRe as implemented in the CCP4 package (Collaborative Computational Project, 1994, The CCP4 suite: programs for protein crystallography, *Acta Crystallogr. D* 50:760-763). Molecular replacement searches with 10- to 4-Å data are carried out by using Fab molecules with a variety of different elbow angles until one (PDB accession code 1RZG (Huang et al., 2004, Structural basis of tyrosine sulfation and VH-gene usage in antibodies that recognize the HIV-1 coreceptor binding site on gp120, *Proc. Natl. Acad. Sci. USA* 101:2706-2711) gave a highly significant translation peak. CNS (Brunger et al., 1998, Crystallography & NMR system: a new software suite for macromolecular structure determination, *Acta Crystallogr. D* 54:905-921) is used for structure refinement, employing simulated torsion angle annealing, standard positional minimization, automated water picking and deletion, low-resolution solvent modeling, and individual restrained isotropic B-value refinement, all aided by interactive model rebuilding in 0 (Jones et al., 1991, Improved methods for building protein models in electron density maps and the location of errors in these models, *Acta Crystallogr. A* 47:110-119) and geometric analysis with Procheck (Laskowski et al., 1993, PROCHECK: a program to check the stereochemical quality of protein structures, *J. Appl. Crystallogr.* 26:283-291) as implemented in CCP4 (Collaborative Computational Project, 1994, The CCP4 suite: programs for protein crystallography, *Acta Crystallogr. D* 50:760-763). The 2F5-$gp41_{660-670}$ 11-mer and 2F5-$gp41_{654-670}$ 17-mer complexes are virtually isomorphous to the 7-mer complex and could be solved by rigid-body refinement. Refinements for the 2F5-11-mer and 2F5-17-mer complexes are carried out as described for the 7-mer.

Sequencing of 2F5.

The published amino acid sequence of 2F5 (Bryson et al., 2001, Cross-neutralizing human monoclonal anti-HIV-1 antibody 2F5: preparation and crystallographic analysis of the free and epitope-complexed forms of its Fab' fragment, *Protein Peptide Lett.* 8:413-418, Kunert et al., 1998, Molecular characterization of five neutralizing anti-HIV type 1 antibodies: identification of nonconventional D segments in the human monoclonal antibodies 2G12 and 2F5, *AIDS Res. Hum. Retroviruses* 14:1115-1128, Pai et al., April 2000, Fab'- epitope complex from the HIV-1 cross-neutralizing monoclonal antibody 2F5, World Intellectual Property Organization patent WO-00/61618.) is confirmed by mass spectroscopy of trypsin-digested 2F5 fragments, which had been purified by reverse-phase chromatography. Peptides with masses that did not agree with the published sequence are characterized by Edman sequencing. In the light chain, one tryptic peptide had an anomalous mass of 1,798.01 Da. This peptide is isolated by high-pressure liquid chromatography and sequenced as SGTASVVCLLNNFYPR (SEQ ID NO: 8), producing a calculated mass of 1,798.038 Da. It differed from the published sequence, SGTASWCLLNNFYPR (SEQ ID NO: 9), by the substitution of two Val residues for one Trp residue. In the heavy chain, one tryptic peptide had a mass difference, being 30 Da heavier than the published sequence. Edman sequencing produced a sequence, GPVNAMDVWGQITVTISSTSTK (SEQ ID NO: 10), which contained an Ala-to-Thr change, accounting for the observed mass difference.

Construction of Env Glycoprotein Expression Plasmids.

A codon-optimized construct of the JRFL gp160 envelope glycoprotein is obtained from the AIDS Research and Reference Reagent Program (Division of AIDS, NIAID, National Institutes of Health [NIH]). To generate JRFL gp145 cleavage-minus, C9-tagged protein, the plasmid is first modified to encode cleavage mutants by replacing two Arg residues at the gp120-gp41 cleavage junction with Ser residues (REKR (SEQ ID NO: 11) to SEKS (SEQ ID NO: 12) at positions 508 and 511). Next, the cleavage-minus mutant, along with the entire transmembrane domain, the first five residues of the cytoplasmic tail, and a C9 tag (TETSQVAPA) (SEQ ID NO: 13), are cloned into the CMV/R vector (Yang et al., 2004, pH-dependent entry of severe acute respiratory syndrome coronavirus is mediated by the spike glycoprotein and enhanced by dendritic cell transfer through DC-SIGN, J. Virol. 78:5642-5650). QuikChange (Stratagene) is used to create expression plasmids encoding variants of the 2F54E10 membrane-proximal region:

```
                                         (SEQ ID NO: 14)
2F5-4E10 (656NEQELLELDKISLWNWFDITNWLWYIK683-
TM-C9 tag), (SEQ ID NO: 14)
HA-2F5-4E10 (HA-656NEQELLELDKISLWNWFDITNWLWYIK
683-TM-C9 tag.), 2F5-HA-4E10 (656NEQELLELDKISL(SEQ ID NO: 15)-HA-
WNWFDITNWLWYIK(SEQ ID NO: 16)683-TM-C9 tag),
and 2F5-4E10-HA (656NEQELLELDKISLWNWFDITNWLW
(SEQ ID NO: 17)-HA-YIK683-TM-C9 tag).
```

HA refers to the hemagglutinin sequence, YPYDVPDYA (SEQ ID NO: 18), which is recognized by the anti-HA antibody sc-7392 (Santa Cruz). The sequences of all constructs are confirmed by DNA sequencing.

Production of HIV-1 EnvPLs.

Expression plasmids are transfected into 293 cells by the calcium phosphate method (Invitrogen). Forty-eight hours after transfection, cells are harvested at 4° C. with phosphate-buffered saline (PBS) containing 5 mM EDTA, washed once with PBS without EDTA, and then used for production of envelope glycoprotein proteoliposomes (EnvPLs), as previously described (Babcock et al., 200%, Ligand binding characteristics of CXCR4 incorporated into paramagnetic proteoliposomes, J. Biol. Chem. 276:38433-38440, Grundner et al., 2002, Solid-phase proteoliposomes containing human immunodeficiency virus envelope glycoproteins, J. Virol. 76:3511-3521). CHAPSO is used for lysis, and 10% glycerol is used in the dialysis buffer. The lipids used are 1-palmitoyl-2-oleoyl-sn-glycero-3-phosphocholine, 1-palmitoyl-2-oleoyl-sn-glycero-3-phosphoethanolamine, and 1,2-dioleoyl-sn-glycero-3-phosphate (Avanti Polar) at a molar ratio of 6:3:1. The presence of the reconstituted lipid membrane is confirmed by staining with R-phycoerythrin-streptavidin (Caltag) and fluorescence-activated flow cytometry. To produce EnvPLs without lipid membrane, EnvPLs are washed extensively with the detergent CHAPSO and then with PBS.

Flow Cytometry Analysis of Antibody Binding.

Anti-HA antibody sc-7392 (Santa Cruz), antibody b12 (D. Burton), and the broadly neutralizing gp41 antibodies 2F5 and 4E10 (H. Katinger) are conjugated with phycoerythrin (M. Roederer, http://www.drmr.com/abcon/) (Roederer et al., 1997, 8 color, 10-parameter flow cytometry to elucidate complex leukocyte heterogeneity, Cytometry 29:328-339). Proteoliposomes (PLs) (106 beads) are separately stained with each of the four phycoerythrin-conjugated antibodies at concentrations ranging from 2 to 200 µg/ml, in a final volume of 100 µl of flow cytometry buffer (PBS containing 3% fetal bovine serum and 0.02% $NaN_3$). All PLs are incubated for 20 min at 4° C., washed twice with flow cytometry buffer, and then analyzed with a FACScan flow cytometer with CellQuest software (Becton Dickinson).

Virus Neutralization Assays.

Virus neutralization data are derived by using CD4 T cells as target cells and flow cytometry to enumerate the number of infected cells after a single round of virus infection (Mascola et al., 2002, Human immunodeficiency virus type I neutralization measured by flow cytometric quantitation of single-round infection of primary human T cells, J. Virol. 76:4810-4821). Briefly, 40 µl of virus stock is incubated with 10 µl of antibody. After incubation for 30 min at 37° C., 20 µl of mitogen-stimulated CD4 T cells ($1.5\times10^5$ cells) is added to each well. The multiplicity of infection is approximately 0.1. Cells are maintained in interleukin-2 culture medium containing 1 µM indinavir and are fed on day 1 with 150 µl of interleukin-2 culture medium. On day 2 after infection, cells are stained for intracellular p24 antigen by using the Beckman Coulter KC57 anti-p24 antibody, followed by quantification of HIV-1-infected cells by flow cytometry. The percentage of neutralization is defined as the reduction in the number of p24-positive cells in antibody-containing wells compared with the number in wells incubated with mock antibody. Virus isolate JRFL is obtained from the NIH AIDS Research and Reference Reagent Program, Division of AIDS, NIAID, NIH.

Structural Analysis and Figure Preparation.

Structural comparisons are made with the CCP4 program lsqkab (Collaborative Computational Project, 1994, The CCP4 suite: programs for protein crystallography, Acta Crystallogr. D 50:760-763). Interactive surfaces are analyzed with MS (Connolly, 1983, Analytical molecular-surface calculation, J. Appl. Crystallogr. 16:548-558), HBPLUS (McDonald and Thornton, 1994, Satisfying hydrogen bonding potential in proteins, J. Mol. Biol. 238:777-793), and Grasp (Nicholls et al., 1991, Protein folding and association: insights from the interfacial and thermodynamic properties of hydrocarbons, Proteins 11:281-296). Figures are made with Grasp (Nicholls et al., 1991, Protein folding and association: insights from the interfacial and thermodynamic properties of hydrocarbons, Proteins 11:281-296), XtalView (McRee, 1999, XtalView/Xfit—a versatile program for manipulating atomic coordinates and electron density, J. Struct. Biol. 125:156-165), and Raster3D (Merritt and Bacon, 1997, Macromolecular crystallography, *Methods Enzymol.* 277:505-524).

Data Deposition.

Coordinates for 2F5 complexed to 7-mer, 11-mer, and 17-mer gp41 peptides have been deposited with the Protein Data Bank under PDB accession codes 1TJG, 1TJH, and 1TJI, respectively.

Results

Crystallization Strategy.

To obtain a structure of 2F5 with its complete gp41 epitope, we adopted an iterative crystallization procedure that allowed us to extend stepwise from the core epitope to encompass the entire 2F5 epitope. We began by trying to reproduce the published 2F5 crystals (Bryson et al., 2001, Cross-neutralizing human monoclonal anti-HIV-1 antibody 2F5: preparation and crystallographic analysis of the free and epitope-complexed forms of its Fab' fragment, *Protein Peptide Lett.* 8:413-418) for their 2F5-7-mer complex. Structure solution and refinement yielded an $R_{crystal}$ of 19.87% and an $R_{free}$ of 22.58% (Table 1). Similar screening is carried out with peptides extending from the core 7-mer an additional three residues on either flank ($gp41_{659-671}$; 13-mer) and an additional six residues on either flank ($gp41_{656-674}$; 19-mer). No crystals are obtained with the 2F5-19-mer complex. Screening with the 2F5-13-mer complex produced crystals with Hampton Crystal Screen reagent 18 (PEG 8000). These crystals are small needles with 622 Laue symmetry and diffracted to only 4 Å.

TABLE 1

Crystallographic data and refinement statistics

| Parameter (unit) | 2F5 Fab + 17-mer-$gp41_{654-670}$ | 2F5 Fab + 11-mer-$gp41_{660-670}$ | 2F5 Fab + 7-mer-$gp41_{662-668}$ |
|---|---|---|---|
| Crystallographic data | | | |
| Space group | $P2_12_12_1$ | $P2_12_12_1$ | $P2_12_12_1$ |
| Unit cell dimensions (Å) | | | |
| a | 58.66 | 58.29 | 57.86 |
| b | 63.68 | 63.52 | 64.02 |
| c | 178.38 | 178.94 | 179.41 |
| Resolution (Å) | 50-2.20 (2.28-2.20) | 50-2.10 (2.18-2.10) | 20-2.00 (2.07-2.00) |
| Reflections (no.) | 204,793 | 254,046 | 175,644 |
| Unique reflections (no.) | 32,958 (2,538) | 38,349 (2,808) | 43,466 (4,039) |
| Completeness (%) | 96.0 (75.5) | 96.4 (72.4) | 97.1 (92.1) |
| I/σ | 14.5 (1.95) | 19.4 (1.57) | 12.5 (1.47) |
| $R_{sym}$ (%)[b] | 12.6 (49.4) | 8.4 (45.1) | 8.9 (53.0) |
| Refinement statistics (F > 0) | | | |
| Nonhydrogen atoms (no.) | | | |
| Total | 4,156 | 3,991 | 3,915 |
| Peptide | 125 | 100 | 60 |
| Solvent | 610 | 470 | 434 |
| Resolution (Å) | 20-2.20 | 20-2.10 | 20-2.00 |
| $R_{crystal}$ (%)[c] | 18.12 | 20.05 | 19.87 |
| $R_{free}$ (%)[c,d] | 22.22 | 23.33 | 22.58 |
| RMSD bond length (Å) | 0.0058 | 0.0057 | 0.0058 |
| RMSD bond angles (°) | 1.320 | 1.374 | 1.333 |
| Avg B factor (Å²) | | | |
| Protein | 31.8 | 39.0 | 29.7 |
| Solvent | 63.6 | 54.8 | 46.1 |

[a]Data in parentheses are for the highest-resolution shell.
[b]$R_{sym} = \Sigma |I_{obs} - I_{avg}|/\Sigma I_{avg}$.
[c]$R = \Sigma_{hkl}||F_{obs}| - |F_{calc}||/\Sigma_{hkl}|F_{obs}|$.
[d]Test set comprised 10% of reflections.

and crystallographic analysis of the free and epitope-complexed forms of its Fab' fragment, *Protein Peptide Lett.* 8:413-418), both alone or in complex with a 7-mer peptide. Perhaps because our 2F5 contained slightly different C termini (produced by endoproteinase Lys-C digestion of alkylated and reduced IgG as opposed to natural digestion), we are unable to reproduce the previous crystals. We used the Hampton Crystal Screen to find alternative crystallization conditions. We are able to grow needles with Hampton Crystal Screen reagent 13 (PEG 400) and to grow diamond plates with reagent 40 (PEG 4000 and isopropanol). The needles did not diffract, whereas the diamond plates diffracted to Bragg spacings of better than 2 Å and turned out to have a lattice similar to that described by Bryson et al. (Bryson et al., 2001, Cross-neutralizing human monoclonal anti-HIV-1 antibody 2F5:

To overcome the sensitivity of complex crystallization to extensions on the core peptide, we proceeded in smaller steps. We extended the 7-mer peptide by one residue on either flank ($gp41_{661}$-669; 9-mer) or by two residues ($gp41_{660-670}$; 11-mer) and tested the 2F5 complexes for crystallization. Diamond plates of the 2F5-11-mer complex could be grown from Hampton Crystal Screen reagent 40 and seeding with the 2F5-7-mer crystals. These 2F5-11-mer crystals diffracted to 2.1 Å, and structure solution and refinement yielded an $R_{crystal}$ of 20.05% and an $R_{free}$ of 23.33% (Table 1). Analysis of the 2F5-11-mer structure showed lattice interactions at the 11-mer C terminus but room to accommodate a longer N terminus. We exploited this information with a 17-mer, $gp41_{654-670}$, which added six residues to the N terminus but left the C terminus intact. This 17-mer encompasses the entire 2F5 epitope, as defined by phage display and protease protection (Parker et al., 2001, Fine definition of the epitope on the gp41 glycoprotein of human immunodeficiency virus type 1 for the neutralizing monoclonal antibody 2F5, *J. Virol.* 75:10906-10911, Zwick et al., 2001, Broadly neutralizing antibodies targeted to the membrane-proximal external region of human immunodeficiency virus type 1 glycoprotein gp41, *J. Virol.* 75:10892-10905), with additional N-terminal residues.

Crystallization of the 2F5-17-mer complex produced diamond shaped crystals with Hampton Crystal Screen reagent 40 after cross-seeding with the 2F5-11-mer crystals. These crystals diffracted to 2.2 Å and are virtually isomorphous with both the 2F5-7-mer and 2F5-11-mer crystals. Structure solution and refinement of the 2F5-17-mer yielded an $R_{crystal}$ of 18.12% and an $R_{free}$ of 22.22% (Table 1), with root-mean square deviations (RMSDs) from ideality on bonds of 0.0058 Å and 87.6% of the residues in the most favored Ramachandran angles. The two Ramachandran outliers, AlaL51 and ThrL30, are typically observed as such in antibodies and occur in well-ordered turns. These outliers are also observed in both the 2F5-7-mer and 2F5-11-mer complexes. Because the 7-mer peptide, $gp41_{654-670}$ (ac-EKNEQELLELD-KISLW-n) (SEQ ID NO: 1), encompassed both the shorter 7-mer and 11-mer peptides, we placed it at the focus of our structural analysis.

Overall Structure of the 2F5-gp41 Complex.

The overall structure of the 2F5 Fab complexed to a 17-mer gp41 epitope is shown in FIG. 1. Main-chain electron density is observed for all 451 residues of the Fab. Density for the heavy chain extended to $Lys_{H218}$ (Kabat IgG numbering) in the hinge region, the predicted cleavage site of the endoproteinase Lys-C used in the Fab preparation. Density for the light chain extended all the way to $Cys_{L214}$, the final light-chain residue. Because reduction and alkylation are performed on the interchain disulfides during preparation of the Fab, $Cys_{L214}$ of the light chain and also CysH216 of the heavy chain are modified by acetamide groups, and these chemical modifications could be observed in the electron density. All six complementarity-determining region (CDR) loops are well ordered, with an average B factor of 26.4 Å$^2$, slightly lower than the average B factor of 31.3 Å$^2$ for the entire Fab. Residue $Gly_{H100c}$ of the 2F5 CDR H3 loop makes a hydrophobic lattice contact with $Arg_{L18}$ of a symmetry mate, while peptide contacts at the base of the CDR H3 appear to be predominantly responsible for ordering the loop, which is disordered when not bound to the epitope (Bryson et al., 2001, Cross-neutralizing human monoclonal anti-HIV-1 antibody 2F5: preparation and crystallographic analysis of the free and epitope-complexed forms of its Fab' fragment, *Protein Peptide Lett.* 8:413-418, Pai et al., April 2000, Fab'-epitope complex from the HIV-1 cross-neutralizing monoclonal antibody 2F5, World Intellectual Property Organization patent WO-00/61618). The relative orientation (elbow angle) between the variable and constant domains is 150.3°.

Figure 2C:
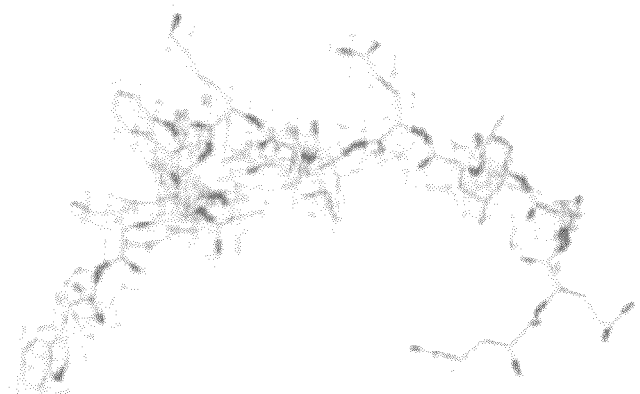
FIG. 2 shows the contact interface between gp41 and 2F5. The orientation shown is similar to that in FIG. 1, Panel B, with the CDR H3 protruding off the top of the figure. Panel A shows the electrostatic potential. An atomic bond representation of the peptide is shown, with gp41 residues labeled. The molecular surface of 2F5 is colored by electrostatic potential: red for electronegative, blue for electropositive, and white for apolar (Nicholls et al., 1991, Protein folding and association: insights from the interfacial and thermodynamic properties of hydrocarbons, *Proteins* 11:281-296). Extensive hydrogen bonds and salt bridges are observed between the peptide and antibody, including contacts with the CDRs of both 2F5 chains, as well as contacts with nonpolymorphic regions of the 2F5 light-chain N terminus. Panel B shows hydrophobic interactions. A representation of the peptide similar to that for Panel A is shown, but in this case it is shown against the $C_\alpha$ worm of the 2F5 heavy and light chains, with side chains labeled and shown in green for 2F5 residues that form hydrophobic contacts with gp41. Panel C shows the electron density of the gp41 peptide. Shown (blue) is the electron density $(2F_o-F_c)$ around the gp41 peptide contoured at $1_\alpha$. The electron density around residues $Glu_{657}$ and $Asn_{658}$ cannot be seen at this contour level, consistent with the tenuous nature of their contacts with 2F5. Beginning with residue $Glu_{659}$, the density improves and is maintained through $Trp_{670}$.
Figure 2B:
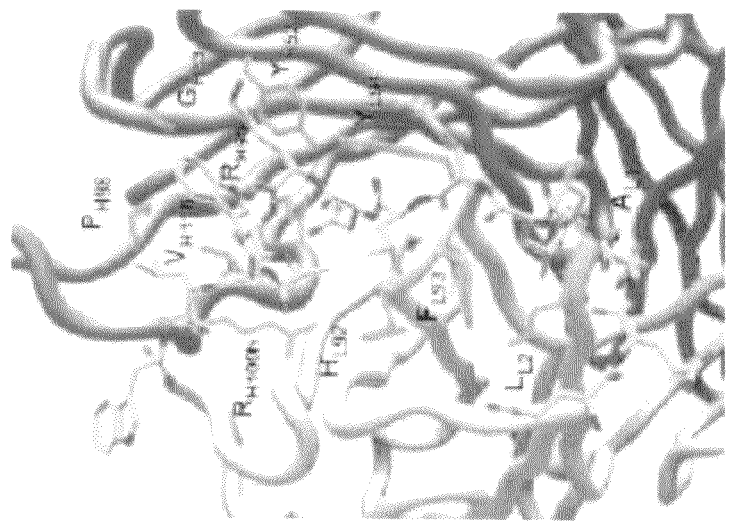
Figure 2A:
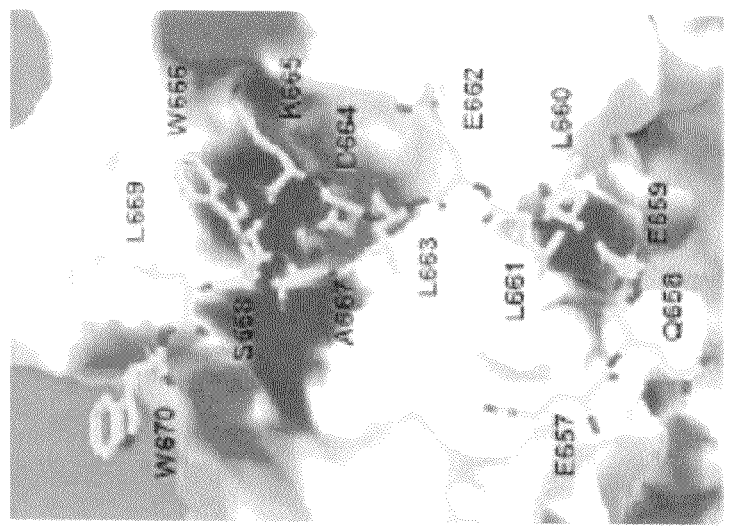

Because we pursued a strategy to visualize the entire 2F5 epitope, the peptide is extended until the N terminus is no longer constrained by interaction with 2F5. Thus, in contrast to the entirely ordered Fab, the first three residues of the gp41 peptide, $Glu_{654}$, $Lys_{655}$, and $Asn_{656}$, could not be discerned, while the next two residues, $Glu_{657}$ and $Gln_{658}$, are marginally ordered. Starting at $Glu_{659}$, the electron density improved, and from $Leu_{660}$ all the way to the C terminus of the peptide at $Trp_{670}$, the structure is clearly defined (FIG. 2, Panel C). This improvement in order is reflected in the B factors, with $Glu_{657}$ and $Gln_{658}$ exhibiting an average B factor of 120.20 Å$^2$, while residues $Glu_{659}$ to $Trp_{670}$ had an average B factor of 35.39 Å$^2$, similar to the average B value of the Fab.

2F5-Bound Conformation of gp41.

The $gp41_{654-670}$ peptide perches in relatively extended conformation at the CDR junction between the heavy and light chains (FIGS. 1 and 2). The peptide spans roughly 25 Å from the C of residue $Glu_{659}$ to the C of $Trp_{670}$, while the maximal side chain distance extends over 30 Å. Progressing from the N terminus, the peptide makes tenuous contact with the CDR L1, bends roughly 90° while passing over and contacting the N terminus of the light chain, and then proceeds in a roughly linear manner 15 Å, past the CDR L3 and H2, with the final seven residues contacting the 22-amino-acid-long CDR H3. The overall extended conformation of the peptide is reflected in its generally B-type Ramachandran angles. Because the peptide N terminus is poorly ordered (FIG. 2, Panel C), it may adopt an alternative conformation in the context of the rest of the envelope ectodomain. Nonetheless, it is noted that the initial bend occurs at a modified gamma-like turn. The carbonyl oxygen of $Gln_{658}$ is outside hydrogen bonding distance (4.9 Å) from the backbone amide of $Leu_{661}$; still, this bend in the peptide allows hydrophobic interactions to occur between the side chains of $Glu_{659}$ and $Leu_{661}$. Within the 14 ordered residues of the peptide, other than the modified gamma-like turn, only two other turns are observed, both of which are type 1 β-turns: one between residues $Asp_{664}$ and $Ala_{667}$ and the other between residues $Trp_{666}$ and $Leu_{669}$. These overlapping turns reverse directional changes, roughly canceling each other so that the overall path of the peptide remains essentially straight (FIGS. 1 and 2). Only three intrapeptide hydrogen bonds occur, one between the backbone amide of $Trp_{666}$ and the side chain carboxylic acid of $Asp_{664}$, one between the backbone amide of $Ala_{667}$ and the carbonyl oxygen of $Asp_{664}$, and one between the backbone amide of $Leu_{669}$ and the carbonyl oxygen of $Trp_{666}$. These intrapeptide hydrogen bonds constrain the conformations of only six residues (residues 664 to 669), suggesting that when excised from the rest of the HIV-1 ectodomain, the conformation of a free gp41 peptide would not be strongly constrained into the conformation recognized by 2F5.

Contact Interface Between gp41 and 2F5.

The overall surface area of 2F5 that is buried by gp41 in the structure is 634.7 Å$^2$, an increase of more than 50% over the area buried by the 7-mer core epitope (418.8 Å$^2$ is buried in the 2F5-7-mer structure). Conversely, the surface area on gp41 that is buried in the interaction with 2F5 is 563.4 Å$^2$ (versus 377.7 A2 in the 2F5-7-mer structure). This falls into the range that is typical for protein-antibody interactions (Davies and Cohen, 1996, Interactions of protein antigens with antibodies, *Proc. Natl. Acad. Sci. USA* 93:7-12). When analyzed according to the chemical nature of the interaction, 43.6% of the interactive surface on the peptide involves non-hydrophobic residues: 28.8% acidic, 11.3% basic, and 3.5% polar. Similarly, many of the residues on the antibody that are buried by gp41 are polar or charged, with 30.7% of the interactive surface contributed by polar residues, 27.6% by basic residues, and 4.8% by acidic residues, with the remaining 36.8% contributed by hydrophobic residues (Table 2). When the surfaces of the antibody and the gp41 peptide are colored by electrostatic potential (FIG. 2, Panel A and FIG. 3, Panel E), their comparison reveals a general complementarity of charge throughout the contact interface.

TABLE 2

Buried surface areas on gp41 and 2F5, by residue

| gp41 residue | Buried surface area (Å²) | 2F5 residue | Buried surface area (Å²) |
|---|---|---|---|
| $Glu_{657}$ | 16.77 | $Ala_{L1}$ | 30.10 |
| $Gln_{658}$ | 19.80 | $Leu_{L2}$ | 14.96 |
| $Glu_{659}$ | 24.26 | $Ser_{L26}$ | 3.59 |
| $Leu_{660}$ | 0 | $Gln_{L27}$ | 45.18 |
| $Leu_{661}$ | 68.18 | $Leu_{L91}$ | 11.77 |
| $Glu_{662}$ | 56.52 | $His_{L92}$ | 41.46 |
| $Leu_{663}$ | 35.65 | $Phe_{L93}$ | 53.37 |
| $Asp_{664}$ | 64.80 | $Tyr_{L94}$ | 70.08 |
| $Lys_{665}$ | 63.63 | $Pro_{L95}$ | 1.97 |
| $Trp_{666}$ | 99.84 | $His_{L96}$ | 9.68 |
| $Ala_{667}$ | 27.98 | $Phe_{H32}$ | 11.20 |
| $Ser_{668}$ | 0 | $Gly_{H33}$ | 27.12 |
| $Leu_{669}$ | 51.60 | $Tyr_{H52}$ | 40.92 |
| $Trp_{670}$ | 34.40 | $Asp_{H54}$ | 16.52 |
| | | $Asp_{H56}$ | 13.98 |
| | | $Arg_{H58}$ | 20.19 |
| | | $Arg_{H95}$ | 28.46 |
| | | $Arg_{H96}$ | 6.51 |
| | | $Gly_{H97}$ | 2.32 |
| | | $Pro_{H98}$ | 32.99 |
| | | $Pro_{H100c}$ | 16.69 |
| | | $Ile_{H100f}$ | 13.42 |
| | | $Ala_{H100g}$ | 20.79 |
| | | $Arg_{H100h}$ | 69.44 |
| | | $Val_{H100k}$ | 26.49 |
| | | $Asn_{H100l}$ | 4.03 |
| Total | 563.42 | Total | 634.74 |

All of the residues of the gp41 peptide between $Gln_{657}$ and $Trp_{670}$, with the exception of $Leu_{660}$ and $Ser_{668}$, interact directly with the antibody, either through hydrogen bonds and salt bridges or through hydrophobic interactions (Tables 2 and 3). These interactions confirm phage display, protease protection, and peptide affinity assays (Barbato et al., 2003, Structural analysis of the epitope of the anti-HIV antibody 2F5 sheds light into its mechanism of neutralization and HIV fusion, *J. Mol. Biol.* 330:1101-1115, Parker et al., 2001, Fine definition of the epitope on the gp41 glycoprotein of human immunodeficiency virus type I for the neutralizing monoclonal antibody 2F5, *J. Virol.* 75:10906-10911, Tian et al., 2002, Structure-affinity relationships in the gp41 ELDKWA (SEQ ID NO: 19) epitope for the HIV-1 neutralizing monoclonal antibody 2F5: effects of side-chain and backbone modifications and conformational constraints, *J. Peptide Res.* 59:264-276, Zwick et al., 2001, Broadly neutralizing antibodies targeted to the membrane-proximal external region of human immunodeficiency virus type I glycoprotein gp41, *J. Virol.* 75:10892-10905) which show that the 2F5 epitope is larger than the originally defined core heptapeptide. At the peptide N terminus, the contacts for the relatively disordered $Glu_{657}$ and $Gln_{658}$ are tenuous, but beginning at $Glu_{659}$, the contact surface becomes well defined, in concordance with peptide affinity assays which show that the presence of $Glu_{659}$ enhances the affinity of 2F5 by six fold (Barbato et al., 2003, Structural analysis of the epitope of the anti-HIV antibody 2F5 sheds light into its mechanism of neutralization and HIV fusion, *J. Mol. Biol.* 330:1101-1115). Unexpectedly, the contact interface between 2F5 and gp41 includes residues not only within the variable CDRs of 2F5 but also within non-polymorphic regions, namely, residues of the N terminus of the light chain. A salt bridge is observed between the side chain carboxylic acid of $Glu_{659}$ and the positively charged light-chain amino terminus, while hydrophobic contacts are observed between the side chain of $Leu_{661}$ and $Ala_{L1}$ and $Leu_{L2}$. These interactions confirm results of binding studies which show that alteration of the 2F5 light-chain N terminus can ablate 2F5's interaction with gp41 (M. Zwick, personal communication), as well as peptide affinity assays which show that extension of the core peptide to $Glu_{659}$ enhances 2F5 affinity (Barbato et al., 2003, Structural analysis of the epitope of the anti-HIV antibody 2F5 sheds light into its mechanism of neutralization and HIV fusion, *J. Mol. Biol.* 330:1101-1115). $Leu_{661}$, which is also critical for optimal 2F5 binding (Tian et al., 2002, Structure-affinity relationships in the gp41 ELDKWA (SEQ ID NO: 19) epitope for the HIV-1 neutralizing monoclonal antibody 2F5: effects of side-chain and backbone modifications and conformational constraints, *J. Peptide Res.* 59:264-276), not only forms interactions with the nonpolymorphic N terminus of the 2F5 light chain but also forms a hydrophobic contact with the side chain of CDR L3 $Phe_{L93}$.

TABLE 3

Hydrogen bonds and salt bridges between gp41 and 2F5

| gp41 residue | 2F5 residue | Distance (Å) |
|---|---|---|
| $Gln_{658}O$ | $Gln_{L27}N\epsilon2$ | 3.18 |
| $Glu_{659}O\epsilon2$ | $Ala_{L1}N$ | 2.88 |
| $Glu_{662}O$ | $Tyr_{L94}N$ | 2.78 |
| $Glu_{662}O\epsilon2$ | $Arg_{H58}NH2$ | 2.76 |
| $Glu_{662}O\epsilon1$ | $Arg_{H58}N\epsilon$ | 2.75 |
| $Asp_{664}O\delta1$ | $His_{L96}N\epsilon2$ | 2.88 |
| $Asp_{664}O\delta1$ | $Arg_{H95}NH1$ | 2.83 |
| $Asp_{664}O\delta2$ | $Arg_{H95}NH2$ | 2.85 |
| $Asp_{664}N$ | $His_{L92}O$ | 2.83 |
| $Lys_{665}N$ | $Tyr_{L94}OH$ | 3.32 |
| $Lys_{665}N\zeta$ | $Asp_{H54}O\delta1$ | 2.75 |
| $Lys_{665}N\zeta$ | $Asp_{H56}O\delta1$ | 2.88 |
| $Trp_{670}O$ | $Arg_{H100h}N$ | 2.89 |

Proceeding further from the peptide N terminus, the gp41 residues $Asp_{664}$, $Lys_{665}$, and $Trp_{666}$, which lie at the core of the 2F5 epitope and have been shown to be essential for 2F5 binding (Conley et al., 1994, Neutralization of divergent human immunodeficiency virus type I variants and primary isolates by IAM-41-2F5, an anti-gp41 human monoclonal antibody, *Proc. Natl. Acad. Sci. USA* 91:3348-3352, Muster et al., 1993, A conserved neutralizing epitope on gp41 of human immunodeficiency virus type 1, *J. Virol.* 67:6642-6647, Purtscher et al., 1996, Restricted antigenic variability of the epitope recognized by the neutralizing gp41 antibody 2F5, *AIDS* 10:587-593), account for over 40% of the surface area that is buried by 2F5 and for almost half of the hydrogen bonds between gp41 and 2F5 (Tables 2 and 3). The side chain of $Asp_664$ makes hydrogen bonds with the guanidinium atoms of CDR H3 $Arg_{1195}$ and the imidazole side chain of CDR L3 $His_{L96}$, while the backbone amide of $Asp_664$ hydrogen bonds with the carbonyl oxygen of CDR L3 $His_{L92}$. These polar interactions are enhanced by hydrophobic interactions between the Cβ of $Asp_{664}$ and the main chain of CDR L3 $His_{L92}$, as well as between the main-chain carbons of $Asp_664$ and the aromatic ring of CDR L3 $Tyr_{L94}$ (FIG. 2, Panel B). $Lys_{665}$ makes hydrogen bonds through its backbone amide and the ring hydroxyl of $Tyr_{L94}$, as well as between its side chain amine and the carboxylic acids of CDR H2 $Asp_{H54}$ and $Asp_{H56}$. The aliphatic base of $Lys_{665}$ is stabilized by packing against the aromatic ring of CDR H2 $Tyr_{H52}$ (FIG. 2, Panel B). Residue $Trp_{666}$, out of all of the gp41 residues, makes the most extensive interactions with 2F5, in terms of buried surface area (Table 2). Its ring carbons make hydrophobic contacts with CDR H1 $Gly_{H33}$, as well as CDR H3 $Arg_{H95}$, $Pro_{H98}$, and $Val_{H100k}$. Taken together, these interactions confirm not only why mutation of these three core gp41 residues ablates 2F5 binding but also why mutations in 2F5 residues (His$_{L92}$, Tyr$_{L94}$, and Phe$_{H32}$) affect binding (Zwick et al., 2004, The long third complementarity-determining region of the heavy chain is important in the activity of the broadly neutralizing anti-human immunodeficiency virus type 1 antibody 2F5, *J. Virol.* 78:3155-3161).

Proceeding further along gp41 toward the 2F5 epitope C terminus, the remaining contacts are made predominantly with the CDR H3, although only with nonapical residues. The side chain of gp$_{41}$ Leu669 interacts with CDR H3 Pro$_{H98}$, confirming its importance for 2F5 binding (Tian et al., 2002, Structure-affinity relationships in the gp41 ELDKWA epitope for the HIV-1 neutralizing monoclonal antibody 2F5: effects of side-chain and backbone modifications and conformational constraints, *J. Peptide Res.* 59:264-276), while the carbonyl oxygen of Trp670 hydrogen bonds with the backbone amide of Arg$_{H100h}$. It is rather surprising that out of the 22 amino acids of the 2F5 CDR H3, only 10 show any interaction with gp41 (Table 2), leaving open the possibility that the 2F5 CDR H3 may have functions outside the realm of direct gp41 binding (see below).

Exclusive 2F5-Bound Face of gp41.

In general, antibodies that bind to peptides envelop them, whereas antibodies that bind to protein surfaces have much flatter surfaces of interaction (Collis et al., 2003, Analysis of the antigen combining site: correlations between length and sequence composition of the hypervariable loops and the nature of the antigen, *J. Mol. Biol.* 325:337-354). In the case of 2F5, out of a total accessible surface area of 1 377 Å$^2$ on the peptide (638.7 Å$^2$ for the core epitope from position 661 to 670), a surface of only 563.4 Å$^2$ (377.7 Å$^2$ for the core) is actually buried by the interaction with 2F5 (FIG. 3, Panels A to C). Thus, only 41% (59% for the core) of the gp41 epitope is buried by 2F5. Instead of enveloping the antigen, 2F5 only binds the gp41 peptide on one exclusive face (FIG. 3, Panels A to C). This mode of interaction is suggestive of an antibody-protein interface in which a non-2F5-bound hidden face is occluded by other portions of the envelope ectodomain.

In order to further address the characteristics of the gp41 peptide surface that is bound by 2F5, as well as the one that is perhaps occluded from 2F5 binding, we analyzed the electrostatic potentials of these surfaces. As shown in FIG. 3, Panels D and E, only the 2F5-bound face of gp41 is charged (FIG. 3, Panel E), while the face that is hidden or occluded from 2F5 binding is much more hydrophobic (FIG. 3, Panel D). The hydrophobicity of this surface provides further support for the possibility that this face of gp41 may be involved in protein contacts which may occlude it from recognition by 2F5. Because antibodies against the hidden hydrophobic face may be preferentially selected due to favorable binding energies at hydrophobic surfaces, this may explain in part why immunizations with non-occluded peptides have thus far failed to elicit 2F5-like antibodies.

Characterization of the 2F5 CDR H3 Loop.

In a survey of human antibodies, the mean length of the CDR H3 loops of antibodies directed against viral antigens is 16.5 residues, which is longer than those of antibodies directed against any other class of antigen (Collis et al., 2003, Analysis of the antigen combining site: correlations between length and sequence composition of the hypervariable loops and the nature of the antigen, *J. Mol. Biol.* 325:337-354). The selection bias for these long loops is not entirely clear, but broadly neutralizing anti-HIV-1 antibodies follow this trend as well, with the CDR H3 loop of 2F5 extending 22 amino acids in length. From analysis of the 2F5-17-mer structure it is clear that the interactions between the CDR H3 loop of 2F5 and gp41 occur predominantly at the base of the CDR H3, while the rest of the residues of the CDR H3, namely, at the apex, remain largely unbound to gp41.

Analysis of the 2F5 CDR H3 loop shows that the apex of the loop (which does not contact gp41) contains a stretch of hydrophobic amino acids, namely, Leu$_{100a}$, Phe$_{100b}$, Val$_{100d}$, and Ile$_{100f}$ (FIG. 4, Panel A). Interestingly, the side chains of these residues all face in the same general direction and define a protruding flat hydrophobic surface (FIG. 4, Panel B). In some ways, the 2F5 CDR H3 resembles the structure of a foot, with the sole of the foot defining a hydrophobic plane.

It has been suggested that D3-3 is the D(H) genomic precursor of this region of 2F5 (Kunert et al., 1998, Molecular characterization of five neutralizing anti-HIV type 1 antibodies: identification of nonconventional D segments in the human monoclonal antibodies 2G12 and 2F5, *AIDS Res. Hum. Retroviruses* 14:1115-1128), in that 13 out of 2F5 CDR H3 nucleotides match with D3-3. If D3-3 is the genomic precursor of this region, then three of the hydrophobic "sole" residues, i.e., Phe$_{100b}$, Val$_{100d}$, and Ile$_{100f}$ would be directly encoded by this D segment. The interspersing proline Pro$_{100e}$ would change during affinity maturation from a D3-3-encoded valine. While valine is compatible with the sole structure, proline with its confining Ramachandran angles serves to restrict conformational flexibility of the loop apex.

Although the hydrophobic apex of the 2F5 CDR H3 does not contact the gp41 peptide directly, the close proximity of the 2F5 epitope to the viral membrane suggests that this hydrophobic surface might interact directly with the viral membrane (FIG. 4, Panel B), or at least allow 2F5 to accommodate an epitope that is in close proximity to the membrane, perhaps by binding to membrane and allowing for enhanced scanning for the gp41 epitope. Perhaps relevant to this, we observed the terminal residue of the 2F5 epitope on gp41, Trp$_{670}$, to be positioned with its hydrophobic indole side chain aligned perfectly with the plane defined by the protruding 2F5 CHR H3 (FIG. 4, Panel B).

Conformation of the 2F5 Epitope within the Context of the Entire Envelope Ectodomain.

The gp41 ectodomain undergoes large conformational changes related to its function as a class I fusion protein (Chan and Kim, 1998, HIV entry and its inhibition, *Cell* 93:681-684). Although we define here the structure of the 2F5 epitope, it is important to further define the context of this structure, both overall, with respect to the fusogenic state of gp41, and locally, with respect to neighboring regions.

In terms of overall conformation, 2F5 is believed to bind optimally to a profusion or intermediate conformation of gp41 (de Rosny et al., 2004, Binding of the 2F5 monoclonal antibody to native and fusion-intermediate forms of human immunodeficiency virus type 1 gp411: implications for fusion-inducing conformational changes, *J. Virol.* 78:2627-2631, Finnegan et al., 2002, Antigenic properties of the human immunodeficiency virus transmembrane glycoprotein during cell-cell fusion, *J. Virol.* 76:12123-12134, Furuta et al., 1998, Capture of an early fusion-active conformation of HIV-1 gp41, *Nat. Struct. Biol.* 5:276-279, Sattentau et al., 1995, Epitope exposure on functional, oligomeric HIV-1 gp41 molecules, *Virology* 206:713-717), although it may also recognize the postfusion six-helix bundle conformation of gp41 (Furuta et al., 1998, Capture of an early fusion-active conformation of HIV-1 gp41, *Nat. Struct. Biol.* 5:276-279, Zwick et al., 2001, Broadly neutralizing antibodies targeted to the membrane-proximal external region of human immunodeficiency virus type I glycoprotein gp41, *J. Virol.* 75:10892-10905). The structure of the prefusion viral spike has not been determined, but several structures of the postfusion six-helix bundle have been determined (Chan et al., 1997, Core structure of gp41 from the HIV envelope glycoprotein, *Cell* 89:263-273, Weissenhorn et al., 1997, Atomic structure of the ectodomain from HIV-1 gp41, *Nature* 387: 426-430). Compared to the six-helix conformation (FIG. 5), which extends to $Lys_{665}$ of gp41 (Weissenhorn et al., 1997, Atomic structure of the ectodomain from HIV-1 gp41, *Nature* 387:426-430), the RMSD of the overlapping main-chain atoms of residues $Glu_{657}$ to $Lys_{665}$ is 3.9 Å$^2$, with numerous steric clashes (FIG. 5). If both the postfusion bundle and the 2F5-bound extended conformation of gp41 are rigidly fixed, these would be incompatible. However, there is considerable flexibility at the overlapping termini of both. The C-terminal region of the six-helix bundle is flexible and susceptible to proteolytic digestion all the way to residue $Leu_{661}$ (Chan et al., 1997, Core structure of gp41 from the HIV envelope glycoprotein, *Cell* 89:263-273), whereas our analysis shows that the 2F5-bound extended conformation of gp41 is not constrained by 2F5 until $Leu_{659}$. Superposition of a truncated HR2 helix (to $Leu_{661}$) with a truncated 2F5 epitope (from $Glu_{659}$) leads to an RMSD of 0.3 Å$^2$, which would be compatible with 2F5 binding, although perhaps at lower affinity.

In terms of the downstream region, NMR analysis of residues $Lys_{665}$ to $Lys_{683}$, in dodecylphosphocholine micelles (Schibli et al., 2001, The membrane-proximal tryptophan-rich region of the HIV glycoprotein, gp41, forms a well-defined helix in dodecylphosphocholine micelles, *Biochemistry* 40:9570-9578), shows an entirely helical conformation (FIG. 5). This would be incompatible with the 2F5-bound structure, with an RMSD for the overlapping six residues (residues 665 to 670) of 1.2 Å$^2$. However, when helices form, unless they encounter a helix-breaking residue or alternative structure, the stability gained by the intrachain hydrogen bonds of the helix often allows them to propagate, extending the helical conformation. Our analysis of the 2F5-bound conformation of gp41 suggests that in the absence of the rest of the gp41 ectodomain, it is held in this conformation primarily by interactions with 2F5. Thus, in the absence of 2F5, it is not unexpected that a helix, formed downstream of the 2F5 epitope, might propagate further upstream. Nonetheless, in light of the many direct contacts of 2F5 in the region of residues 661 to 670 (FIG. 2), and because 2F5 can bind to the membrane-proximal region of gp41 in the presence of lipid, when 2F5 is bound, we would expect the region of residues 661 to 670 to adopt the extended conformation that we observe in the 2F5-gp41 crystal structure. Taken together, the data suggest that the membrane-proximal region at the start of the 2F5 epitope is relatively flexible, perhaps assuming different conformations depending on the fusogenic state of gp41. From the center to the end of the 2F5 epitope (residues 661 to 670), an extended mostly β conformation, containing two overlapping type 1 β-turns, stretches for roughly 25 Å. In the prefusogenic state, this extended structure is presumably stabilized by interactions through its hidden face with the rest of the HIV ectodomain. Then, from residues 670 to 683, a hydrophobic helix, perhaps lying parallel with the viral membrane (Scbibli et al., 2001, The membrane-proximal tryptophan-rich region of the HIV glycoprotein, gp41, forms a well-defined helix in dodecylphosphocholine micelles, *Biochemistry* 40:9570-9578), would complete the ectodomain (FIG. 6).

Binding of 2F5 to gp41 is Enhanced by Lipid Membrane and Hydrophobic Context.

The structural model (FIG. 6) predicts that proper formation of the 2F5 and 4E10 epitopes should be strongly dependent on the presence of membrane. In order to confirm biochemically that an intimate association exists between the membrane-proximal region of gp41 and the viral membrane, we performed binding studies using PLs in which various envelope constructs are presented in either the presence or absence of lipid membrane. As shown in FIG. 7, Panel A, when JRFL gp145 is presented on PLs in the presence of lipid, the affinity of both 2F5 and 4E10 increased. In contrast, the presence of lipid had no effect on the affinity of the anti-gp120 antibody b12.

To confirm that antibody binding to membrane-proximal epitopes is not merely inhibited by aggregation or large-scale structural rearrangement of the transmembrane region in the absence of lipid, we interspersed the HA antibody epitope into three different locations of the membrane-proximal region: at the N terminus of the 2F5 epitope, between the 2F5 and 4E10 epitopes, and downstream of the 4E10 epitope (FIG. 7, Panel B). With the exception of 2F54E10-HA, which displayed lower anti-HA antibody binding regardless of the presence of lipid, the binding of the HA antibody to the constructs is not affected by the presence of lipid (FIG. 7, Panel B). Binding of 2F5, however, to HA-2F5-4E10 and 2F5-4E10-HA increased in the presence of lipid, as did binding of 4E10 to HA-2F54E10 and 2F5-HA-4E10 (FIG. 7, Panel B). These results suggest that the membrane-proximal region of these constructs is accessible even in the absence of membrane and that the lower binding affinity of 2F5 and 4E10 to gp41 after the loss of lipid is not an artifact but rather is an actual effect of the loss of a hydrophobic binding environment.

In addition to the presence of membrane, these studies also suggest that the hydrophobic continuity of the membrane-proximal region is an important factor in optimal 2F5 binding. In construct 2F5-HA4E10 (FIG. 7, Panel B), where an HA tag disrupts the continuity of the membrane-proximal region by being placed between the 2F5 and 4E10 epitopes, the effect of enhanced membrane context 2F5 affinity is decreased. The membrane context effect is recovered, however, when the HA tag is placed downstream of the 4E10 epitope and continuity is restored (FIG. 7, Panel B). These results may be due to the fact that when Trp670, which is predicted from our structural analysis to lie along the plane of the viral membrane (FIG. 4), is displaced from the core 2F5 epitope by an HA tag, the 2F5 epitope, and therefore 2F5 itself, is not sufficiently close to the membrane for the hydrophobic CDR H3 of 2F5 to fully enhance binding. Taken together, these biochemical analyses confirm the structural model that the membrane-proximal region of gp41 is intimately involved with the viral membrane and that the integrity of the 2F5 and 4E10 epitopes is highly membrane- and sequence-context dependent. Because the viral membrane is derived from host lipids, it is seen as self by the immune system. Such an intimate membrane association with the viral envelope may help to obscure humoral immune recognition; the membrane-proximal region would "sit" on the membrane, restricting steric accessibility to otherwise conserved potential neutralization epitopes. In this context we note that an examination of viral envelope class I fusion proteins shows that many of the lentiviruses, which form persistent infections, have similar long hydrophobic membrane-proximal regions after their HR2 helices. In contrast, for nonpersistent infections such as influenza and Ebola virus infections, the membrane-proximal regions are much less hydrophobic, while those of morbillivirus (measles) and rubulavirus (mumps) are far shorter.

Large-Scale Steric Accessibility.

Because 2F5 and 4E10 do not block gp120-receptor interactions, these antibodies may bind after virus-cell surface attachment. But in order to do so, they might face steric barriers related to this crowded interface, as has been observed with CD41 antibodies, where steric constraints preclude IgG binding (Labrijn et al., 2003, Access of antibody molecules to the conserved coreceptor binding site on glycoprotein gp120 is sterically restricted on primary human immunodeficiency virus type 1, *J. Virol.* 77:10557-10565). Thus, we sought to address whether the membrane-proximal region of gp41 is subject to any large-scale steric hindrances.

For this purpose, we compared the neutralization capacities of the Fab versus the IgG for the respective antibodies. Since a Fab is approximately one-third the size of an IgG, if large-scale steric clashes that hinder binding occur, then one would expect the Fab to neutralize better than the IgG, as is the case for the CD41 antibodies that bind at the sterically restricted virus-cell interface (Labrijn et al., 2003, Access of antibody molecules to the conserved coreceptor binding site on glycoprotein gp120 is sterically restricted on primary human immunodeficiency virus type 1, *J. Virol.* 77:10557-10565). In general, however, for antibodies that are not sterically restricted, Fabs neutralize less well than the bulkier bivalent IgGs. As shown in FIG. 8, the 2F5 and 4E10 Fabs (FIG. 8, Panels A and B), as well as the gp120-reactive b12 Fab (FIG. 8, Panel C), are less effective than their respective IgGs in neutralizing the primary HIV-1 strain JRFL, suggesting that 2F5 and 4E10 are not affected by large-scale steric hindrance of IgG access to the membrane-proximal region.

Vaccine Implications.

The findings of this study suggest that an effective immunization strategy to elicit 2F5- or 4E10-like broadly neutralizing antibodies would likely have to account for viral mechanisms of immune evasion that constrain the membrane-proximal region, namely, conformation, surface occlusion, and membrane proximity, although perhaps not large-scale steric accessibility. The precise conformation that 2F5 recognizes may be difficult to stabilize. Both the upstream six-helix bundle and downstream membrane-bound helix enforce different conformations on the 2F5 epitope. The stabilization of extended structures is also not trivial. Tight turns can be stabilized with designed disulfide or lactam bridges (FIG. 9, Panel A), and such approaches are already under way (McGaughey et al., 2003, HIV-1 vaccine development: constrained peptide immunogens show improved binding to the anti-HIV-1 gp41 MAb, *Biochemistry* 42:3214-3223, Tian et al., 2002, Structure-affinity relationships in the gp41 ELDKWA (SEQ ID NO: 19) epitope for the HIV-1 neutralizing monoclonal antibody 2F5: effects of side-chain and backbone modifications and conformational constraints, *J. Peptide Res.* 59:264-276); even so, such turns account for less than half of the 2F5 epitope. One critical question will be the degree of flexibility of the 2F5 epitope in the context of the full envelope ectodomain. Does the entire 2F5-bound conformation observed in this structure have to be stabilized, or is only a critical substructure essential for broad immune recognition? Such questions should be answerable by immunizations with structurally constrained antigens. Alternatively, structures of the 2F5 epitope in a more complete ectodomain context, or even in complex with another neutralizing antibody that recognizes the 2F5 epitope, may also provide answers.

To account for local surface occlusion, immunogens that induce antibodies that only bind to the 2F5-bound surface would need to be designed. This might be accomplished in a manner similar to that tried for anti-gp120 immunogens, for example, by masking the unbound hidden surface of gp41 with carbohydrate modifications (FIG. 9, Panel B) (Pantophlet et al., 2003, Hyperglycosylated mutants of human immunodeficiency virus (HIV) type I monomeric gp120 as novel antigens for HIV vaccine design, *J. Virol.* 77:5889-5901). O-linked glycosylation might be preferable in this case due to the smaller size of these glycans, which would interfere less with the 2F5-bound face of the peptide. Alternatively, one could anchor the epitope to a larger molecule or surface in a manner that would leave only the 2F5-bound surface exposed. For example, one could first attach reactive groups on to the hidden face of the gp41 epitope, then bind the 2F5 complex to a nonimmunogenic graphite or plastic surface that reacts with these groups, and then release 2F5. The latter approach not only would eliminate local surface occlusion but also would allow the reactive groups to weld the 2F5-enforced conformation into place.

In terms of membrane proximity, one could present a conformationally stabilized, surface-occluded immunogen in the context of membrane, either on virus-like particles or on PLs (Grundner et al., 2002, Solid-phase proteoliposomes containing human immunodeficiency virus envelope glycoproteins, *J. Virol.* 76:3511-3521) (FIG. 9, Panel C). The enhanced 2F5 binding that we observed in the context of a PL membrane (FIG. 7) suggests that even in a highly artificial context, the presence of membrane recapitulates essential components of 2F5 and 4E10 recognition.

Elicitation of 2F5-like antibodies with any of these immunogens could be enhanced with prime-boost strategies (FIG. 9, Panel D). For example, priming with a conformationally stabilized, surface-occluded, membrane-anchored immunogen may elicit high titers of antibodies, only a small portion of which recognize virus. A boost, on the other hand, composed of the complete wild-type envelope ectodomain and presented in a membrane-anchored context, should select antibodies capable of binding wild-type virus. Such prime-boost strategies could be repeated (for example, with diverse strains of HIV or with additional peptides) to enhance antibody specificity and titer.

These immunization strategies (FIG. 9) should account for the constraints on the conserved membrane-proximal epitope suggested by our mechanistic analysis of the 2F5-gp41 crystal structure. Whether the analysis presented here defines a sufficient road map for elicitation of 2F5- or 4E10-like antibodies will need to be determined experimentally. Our studies on 2F5 and those of others on b12 and 2G12 (Calarese et al., 2003, Antibody domain exchange is an immunological solution to carbohydrate cluster recognition, *Science* 300:2065-2071, Saphire et al., 2001, Crystal structure of a neutralizing human IGG against HIV-1: a template for vaccine design, *Science* 293:1155-1159, Zwick et al., 2001, Broadly neutralizing antibodies targeted to the membrane-proximal external region of human immunodeficiency virus type I glycoprotein gp41, *J. Virol.* 75:10892-10905) present a paradigm for using structural information from broadly neutralizing antibodies to understand and overcome HIV-1 mechanisms of immune evasion.

Example 2

Examples of Immunogen Platforms

Three examples of immunogen platforms are shown in FIG. 10. Panels A and B show schematic illustrations of the results of immunizations with nucleic acid molecules (i.e. genetic immunizations) that encode the 2F5 epitope in association with the 4E 10 & Z13 epitopes, a transmembrane domain, and a heterologous protein X (Panel A) or gp41 ectodomain sequence (Panel B) that have been designed for desired presentation of the 2F5 epitope. FIG. 10, Panel C is a schematic representation of a 2F5 peptide immunogen, wherein the peptide has been designed for the desired presentation of the 2F5 epitope.

Potential gp41 constructs for genetic immunization are outlined below:

"26mer" refers to the membrane proximal region of gp41 from NEQ through the 4E10 epitope to the putative beginning of the transmembrane domain (NEQELLELDKWASLWNWFNITNWLWYIK (SEQ ID NO: 20)

"CD5 leader" refers to the leader sequence of the CD5 scavenger receptor protein.

"C9" refers to short peptide epitope tag which can be recognized by the 1D4 antibody. C9 is added for PL capture and will not interfere with genetic expression—His capture is a potential improvement, as are varying the lipid ratios "PADRE" refers to a T-helper epitope (pan DR epitope ("PADRE")) described in WO 95/07707 and in the corresponding paper Alexander J et al., 1994, Immunity 1: 751-761

"TM" refers to the transmembrane domain of gp41.

"Foldon" refers to the Foldon Domain of Bacteriophage T4 Fibritin.

Category A: T-Cell Help
1. CD5 leader-PADRE-28mer-TM-C9
2. CD5 leader-28mer-TM-PADRE-C9
3. CD5 leader-PADRE-28mer-TM-PADRE-C9

Blend to Add Hydrophobic Patch (Arbitrary Sequence)
4. CD5 leader-PADRE-GG-WYWY-GG-28mer-TM-C9

Category B: Trimerization
5. CD5 leader-28mer-TM-GGG-foldon-C9
6. CD5 leader-PADRE-28mer-TM-GGG-foldon-C9

Category C: Membrane Interaction
7. CD5 leader-CAAX-G-28mer-TM-C9
8. CD5 leader-CD4 TM-28mer-TM-C9
9. CD5 leader-CD4 TM-G4S spacer-28mer-TM-C9
10. CD5 leader-fusion peptide-28mer-TM-C9

Category D: Repeat Strategy
11. CD5 leader-28mer-28mer-TM-C9
12. CD5 leader-28mer-28mer-28mer-TM-C9

Category E: Upstream Sequence
13. CD5 leader-C34-28mer-TM-C9
14. CD5 leader-N36-28mer-TM C9

Example 3

Analysis of 2F5 Antibody Sequence Homology with Other Immunoglobulins

The nucleotide sequence of the heavy chain variable region of the 2F5 antibody is used as query sequence find homologous immunoglobulins. The following immunoglobulins are identified: X69690; L21964; X62111; L21972; L21968. This analysis reveals that the 2F5 antibody has a high degree of sequence homology with autoreactive antibodies, especially with an anti-cardiolipin antibody X69690 (AF455551), which also utilizes the D3-3 D segment germline gene. The sequences of polynucleotides encoding these genes is shown below:

```
Input
                                        (SEQ ID NO: 21)
agg atc acg tta aag gaa tcg ggt cct ccg ctg gtg
aaa ccc aca cag act ctc acg ctg acc tgt tcc ttc
tct ggg ttc tca ctg tcc gat ttt gga gtg ggt gtg
ggc tgg atc cgt cag ccc cca gga aag gcc cta gag
tgg ctt gca atc att tat tcg gat gat gat aag cgc
tac agc cca tcg ctg aac acc aga ctc acc atc acc
```

-continued

```
aag gac acc tcc aaa aat caa gtt gtc ctt gtc atg
act agg gtg agt cct gtg gac aca gcc acg tat ttc
tgt X69690-IGVH2-5*10
                                        (SEQ ID NO: 22)
cag atc acc ttg aag gag tct ggt cct acg ctg gtg
aaa ccc aca cag acc ctc acg ctg acc tgc acc ttc
tct ggg ttc tca ctc agc act agt gga gtg ggt gtg
ggc tgg atc cgt cag ccc cca gga aag gcc ctg gag
tgg ctt gca ctc att tat tgg gat gat gat aag cgc
tac agc cca tct ctg aag agc agg ctc acc atc acc
aag gac acc tcc aaa aac cag gtg gtc ctt aca atg
acc aac atg gac cct gtg gac aca gcc aca tat tac
tgt L21964-IGVH2-5*05
                                        (SEQ ID NO: 23)
cag atc acc ttg aag gag tct ggt cct acg ctg gtg
aaa ccc aca cag acc ctc acg ctg acc tgc acc ttc
tct ggg ttc tca ctc agc act agt gga gtg ggt gtg
ggc tgg atc cgt cag ccc cca gga aag gcc ctg gag
tgg ctt gca ctc att tat tgg gat gat gat aag cgc
tac ggc cca tct ctg aag agc agg ctc acc atc acc
aag gac acc tcc aaa aac cag gtg gtc ctt aca atg
acc aac atg gac cct gtg gac aca gcc aca tat tac
tgt X62111-IGVH2-5*01
                                        (SEQ ID NO: 24)
cag atc acc ttg aag gag tct ggt cct acg ctg gtg
aaa ccc aca cag acc ctc acg ctg acc tgc acc ttc
tct ggg ttc tca ctc agc act agt gga gtg ggt gtg
ggc tgg atc cgt cag ccc cca gga aag gcc ctg gag
tgg ctt gca ctc att tat tgg aat gat gat aag cgc
tac agc cca tct ctg aag agc agg ctc acc atc acc
aag gac acc tcc aaa aac cag gtg gtc ctt aca atg
acc aac atg gac cct gtg gac aca gcc aca tat tac
tgt L21972-IGVH2-5*09
                                        (SEQ ID NO: 25)
cag gtc acc ttg aag gag tct ggt cct acg ctg gtg
aaa ccc aca cag acc ctc acg ctg acc tgc acc ttc
tct ggg ttc tca ctc agc act agt gga gtg ggt gtg
ggc tgg atc cgt cag ccc cca gga aag gcc ctg gag
tgg ctt gca ctc att tat tgg gat gat gat aag cgc
tac ggc cca tct ctg aag agc agg ctc acc atc acc
aag gac acc tcc aaa aac cag gtg gtc ctt aca atg
acc aac atg gac cct gtg gac aca gcc aca tat tac
tgt L21968-IGVH2-5*10
                                        (SEQ ID NO: 26)
cag atc acc ttg aag gag tct ggt cct acg ctg gtg
aaa ccc aca cag acc ctc acg ctg acc tgc acc ttc
tct ggg ttc tca ctc agc act agt gga gtg ggt gtg
ggc tgg atc cgt cag ccc cca gga aag gcc ctg gag
tgg ctt gca ctc att tat tgg aat gat gat aag cgc
tac agc cca tct ctg aag agc agg ctc acc atc acc
aag gac acc tcc aaa aac cag gtg gtc ctt aca atg
acc aac atg gac cct gtg gac aca ggc aca tat tac
tgt
```

The alignment of polynucleotides encoding these immunoglobulins is shown in FIG. 15 (Panels A and B).

These results indicate that a useful approach to generation of 2F5-like anti-HIV neutralizing antibodies is to present a gp41 membrane proximal immunogen in a membrane/proteoliposome context wherein the membrane context differs from the normal membrane context of the outer plasma membrane. For example, the membrane context might be varied to include different ratios of lipids or to include cardiolipin, or other lipids that are not normally found on the outer plasma membrane.

Example 4

Genetically Based Protein Scaffolds for gp41 Membrane Proximal Region Immunogens An immunogen that can fit into a genetic platform and elicit 2F5- and 4E10-like broadly neutralizing anti-HIV antibodies is designed. Structural analysis of the 2F5 antibody in complex with the membrane-proximal region of the gp41 ectodomain indicated two components in 2F5 antibody binding of the membrane proximal region of gp41: The first component is a specific high affinity interaction with the gp41 protein. The second component is a non-specific direct interaction between the hydrophobic apex of the 2F5 CDRH3 loop with the viral membrane. The structural analysis of the binding interaction also indicated that a charged face of the gp41 membrane proximal region is exclusively bound by 2F5, while a non-bound highly hydrophobic face may be occluded in the larger native spike. Thus, the design of an immunogen capable of eliciting 2F5- and 4E10-like antibodies may incorporate the following three factors:
1) Structural stabilization of the immunogen into the conformation of the membrane proximal region when bound to 2F5 or 4E10.
2) Occlusion of the non-2F5-bound hydrophobic face of the gp41 membrane proximal region.
3) Presentation of the conformationally stabilized, surface occluded immunogen in the context of a membrane.

One strategy for the initial modeling of a "genetic platform" for the immunogen is a strategy is based on the use of a structural homology search. No hits are obtained using the dali server when the 2F5-bound peptide structure is queried, or when any of five different extended structures (extended to include the downstream region of gp41 that is bound by the 4E10 antibody (using a published NMR structure of that region) at five different angles) are queried. In essence, a helical extension is modeled at five different angles, all having the helix lying horizontally along the external surface of the viral membrane. A program called grath also does not yield hits when queried with the 2F5-bound peptide structure, but does yield hits when queried with the five extended peptide structures. Four out of the five extended structures yield identical hits while one (at 90 degrees) yield some unique hits. The results of queries in grath with the extended structures are shown in Tables 4 and 5 below.

TABLE 4

GRATH results for 90

| Rank | PDB id | Fold | Description | Method | Score |
|---|---|---|---|---|---|
| 1 | 1k8vA0 | 8.1.204 | neuropeptide f | NMR | 0.243 |
| 2 | 2occL0 | 4.10.49 | Bovine heart cytochromE C oxidase at the fully oxidized state | XTAL | 0.01 |
| 3 | 1gdtA2 | 1.20.5 | site-specific recombinase | XTAL | 0.084 |
| 4 | 1igBA1 | 7.2.17 | yeast hexokinase pii | XTAL | 0.772 |
| 5 | 1h9eA0 | 6.1.143 | Lem-like domain of human inner nuclear membrane protein lap2 | NMR | 0.832 |
| 6 | 1kekA4 | 4.10.780 | free radical intermediate of pyruvate:ferredoxin oxidoreductase | XTAL | 0.865 |
| 7 | 1onvB0 | 8.1.695 | complex containing the tfiif subunit rap74 and the map ii ctd phosphatase fcp1 | NMR | 0.868 |
| 8 | 1p3qR0 | 8.1.763 | cue domain of vps9 | XTAL | 0.874 |
| 9 | 1erd00 | 1.10.10 | Pheromone er-2 | NMR | 0.881 |

TABLE 4-continued

GRATH results for 90

| Rank | PDB id | Fold | Description | Method | Score |
|---|---|---|---|---|---|
| 10 | 1j09A4 | 1.10.8 | thermus thermophilus glutamyl-tRNA synthetase complexed with atp and glu | XTAL | 0.888 |

TABLE 5

GRATH Results for 0, 45, 135, 180

| Rank | PDB id | Fold | Description | Method | Score |
|---|---|---|---|---|---|
| 1 | 1gnf | 3.30.50.10 | n-terminal zinc finger of murine gata-1 | NMR | −0.039 |
| 2 | 1kek | 4.10.780 Chain A, domain 4 | free radical intermediate of pyruvate:ferredoxin oxidoreductase | XTAL | 0.061 |
| 3 | 1a81 | 1.10.930.10 Syk Kinase; orthogonal fold | tandem sh2 domain of the syk kinase bound to a dually tyrosine-phosphorylated itam | XTAL | 0.128 |
| 4 | 1byy | 1.20.5.150 | Sodium channel iia inactivation gate | NMR | 0.231 |
| 5 | 1onv | 8.1.695 | complex containing the tfiif subunit rap74 and the map ii ctd phosphatase fcp1 | NMR | 0.316 |
| 6 | 1erd | 1.10.10 Arc Repressor Mutant, subunit A | Pheromone er-2 | NMR | 0.374 |
| 7 | 1p3q | 8.1.763 | cue domain of vps9 | XTAL | 0.426 |
| 8 | 2occ | 4.10.95 Cytochrome C Oxidase; Chain G | Bovine heart cytochromE C oxidase at the fully oxidized state | XTAL | 0.44 |
| 9 | 1g72 | 4.10.160 | Oxidoreductase; Catalytic mechanism of quinoprotein methanol dehydrogenase. | XTAL | 0.491 |
| 10 | 1hdl | 6.1.157 | Putative serine proteinase inhibitor | XTAL | 0.491 |

A second strategy for the initial modeling of a "genetic platform" for the immunogen is a strategy that employs a search of the known structures of integral membrane proteins and the identification of any motifs that might mimic or present a good platform for inserting the membrane proximal immunogen. The known structures of membrane proteins are examined to determine if the loop-helix motif of the gp41 membrane proximal region could be easily inserted, or if such a motif already exists on the surface of one of these proteins. The website World Wide Web at blanco.biomol.uci.edu/Membrane Proteins xtal.html which has a comprehensive list of known integral membrane protein structures, as well as links to relevant references, is employed. Since many of the structures are similar based on the class to which they belong, the list is categorized accordingly, and approximately 75-100% of the structures in each category are searched qualitatively. In general, four elements are searched for in the structures: 1) the presence of extracellular loop-helix motifs that mimic the structure of the membrane proximal region of gp41; 2) the presence of extracellular loops which can be substituted with the 2F5/4E10 immunogen; 3) whether the structures provide an adequate "membrane context" for the gp41 immunogen; 4) whether the structures provide a possible mechanism for occluding the non-2F5-bound face of the membrane proximal region.

Six structures, based on category, are selected which appear to be tractable for use as a platform for insertion and further optimization of the gp41 membrane proximal immunogen. They are as follows: (1) the potassium channels, (2) SecYE protein conducting channel, (3) photosynthetic reaction center, (4) Cytochrome bc1 complex, (5) bacterial rhodopsin, and (6) beta-barrel membrane proteins (porins and relatives). In general, the identified structures fall into two groups: those that contain a semblance of a loop-helix motif on the membrane surface (with the helix lying horizontally on the membrane surface), and those that just contain a loop on the membrane surface. The structures of the Cytochrome bc1 complex, potassium channel, SecYE protein conducting channel, and the photosynthetic reaction center all contain some form of a loop-helix motif, while the bacterial rhodopsins and beta-barrel membrane proteins just contain extracellular loops that appear large enough to accommodate an insertion. Detailed notes on each the identified structures are provided below.

1) Potassium Channels (sample pdb ids: 1K4C, 1K4D, 1LNQ): These are very compact structures with only 4 transmembrane domains. The transmembrane helix Ml connects through an extracellular loop to a semi-horizontal "pore helix".
2) SecYE&beta protein conducting channel (1RHZ): These structures contain an extracellular loop which then connects to a semi-helix before reentering the membrane. These structures may provide sufficient space for gp41 loop-helix.
3) Photosynthetic reaction center (1OGV): This structure has a number of horizontal helices on the periplasmic face of the membrane which could mimic 4E10-bound helix.
4) Cytochrome bc1 complex (1QCR): A transition from A TM to B TM, which has a loop and a horizontal helix, is recommended. Additionally, a transition from C to D-helix, which contains horizontal helix CD1, is also recommended.
5) Bacterial Rhodopsins (sample protein database IDs: 1AP9, 1QJH, 1C3W): These structures are 7 transmembrane domain proteins, and are trimeric. In structure 1AP9, the extracellular loops BC, DE, and FG appear large enough to accommodate the 2F5 epitope immunogen, and provide adequate membrane context.
6) Beta-barrel membrane proteins (Porins and relatives; sample protein database IDs: 2MPR, 1BXW): The structure 2 MPR is a porin with extracellular loops of varying lengths. Loops L6 and L9 appear large enough to accommodate the immunogen. Structure 1BXW is an outer membrane protein (OmpA), which is more compact than the porins, with fewer transmembrane beta-strands. Loops L1 and L4 of this structure are good candidates for immunogen insertion. For porin structures in general, intracellular loops should be sufficiently close to membrane surface; in some cases the beta barrels extend far beyond the surface and may not provide adequate membrane context.

Example 5

Rationally Designed Genetic Immunogen Constructs

Figure 11:
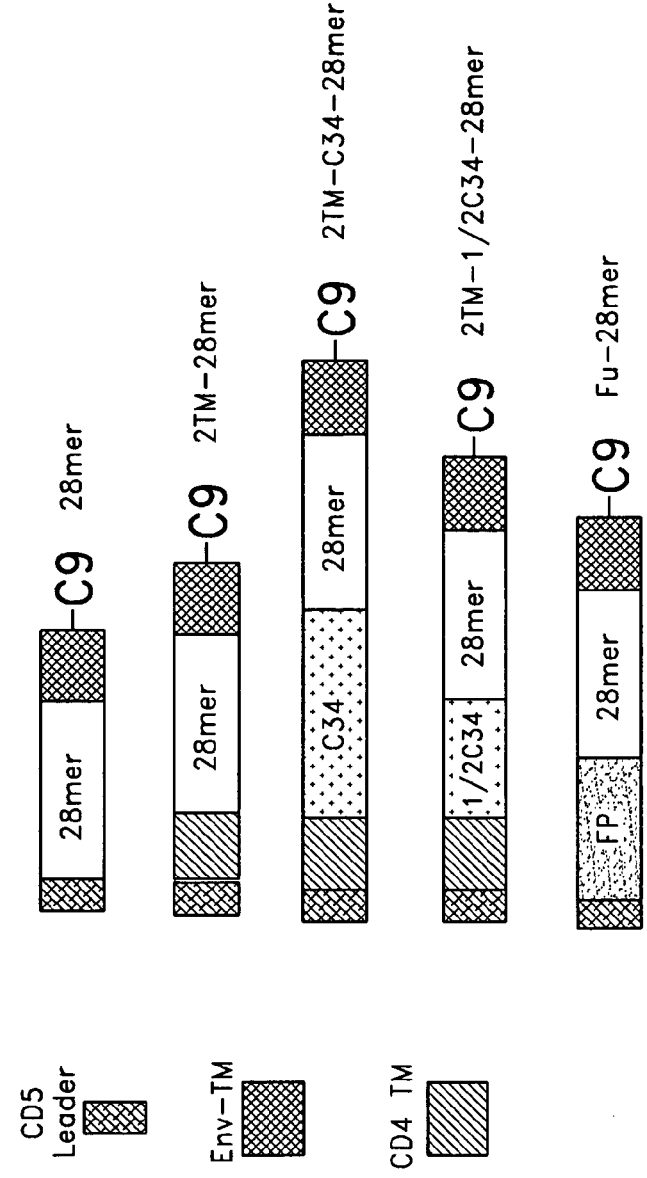

A set of gp41 constructs were rationally designed based on the 28mer construct: NEQELLELDKWASLWNWFNIT-NWLWYIK (SEQ ID NO: 20) (FIG. 11)

Figure 12:
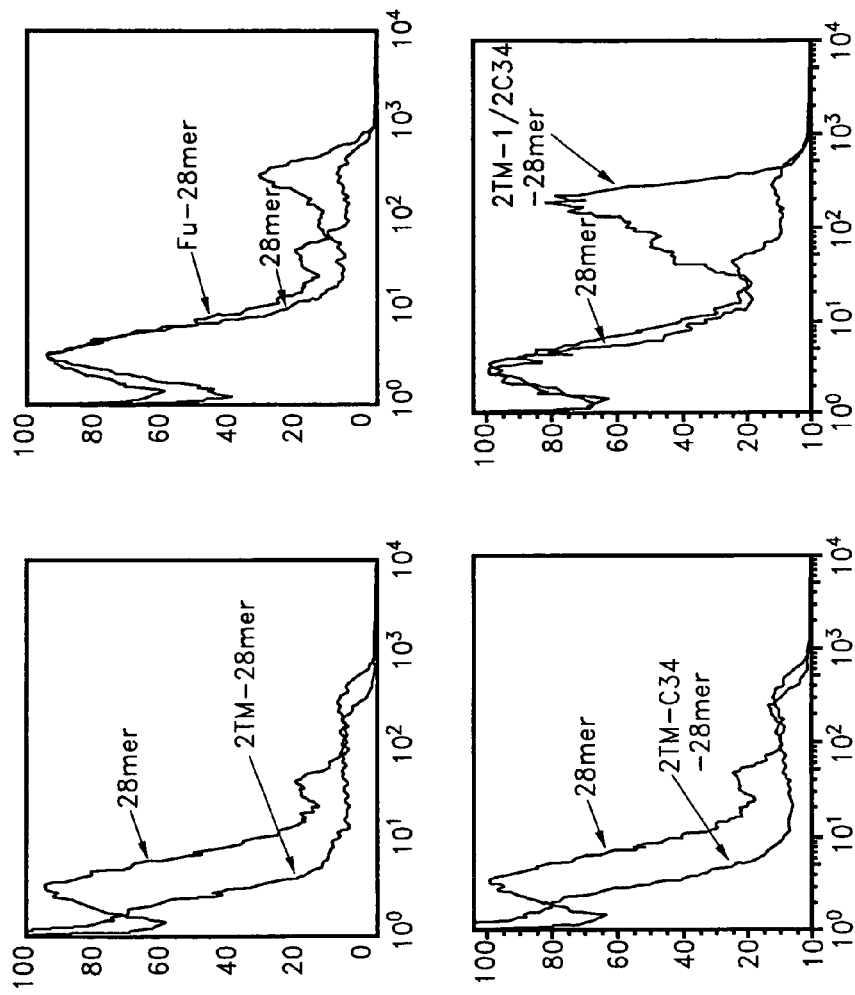
Figure 13:
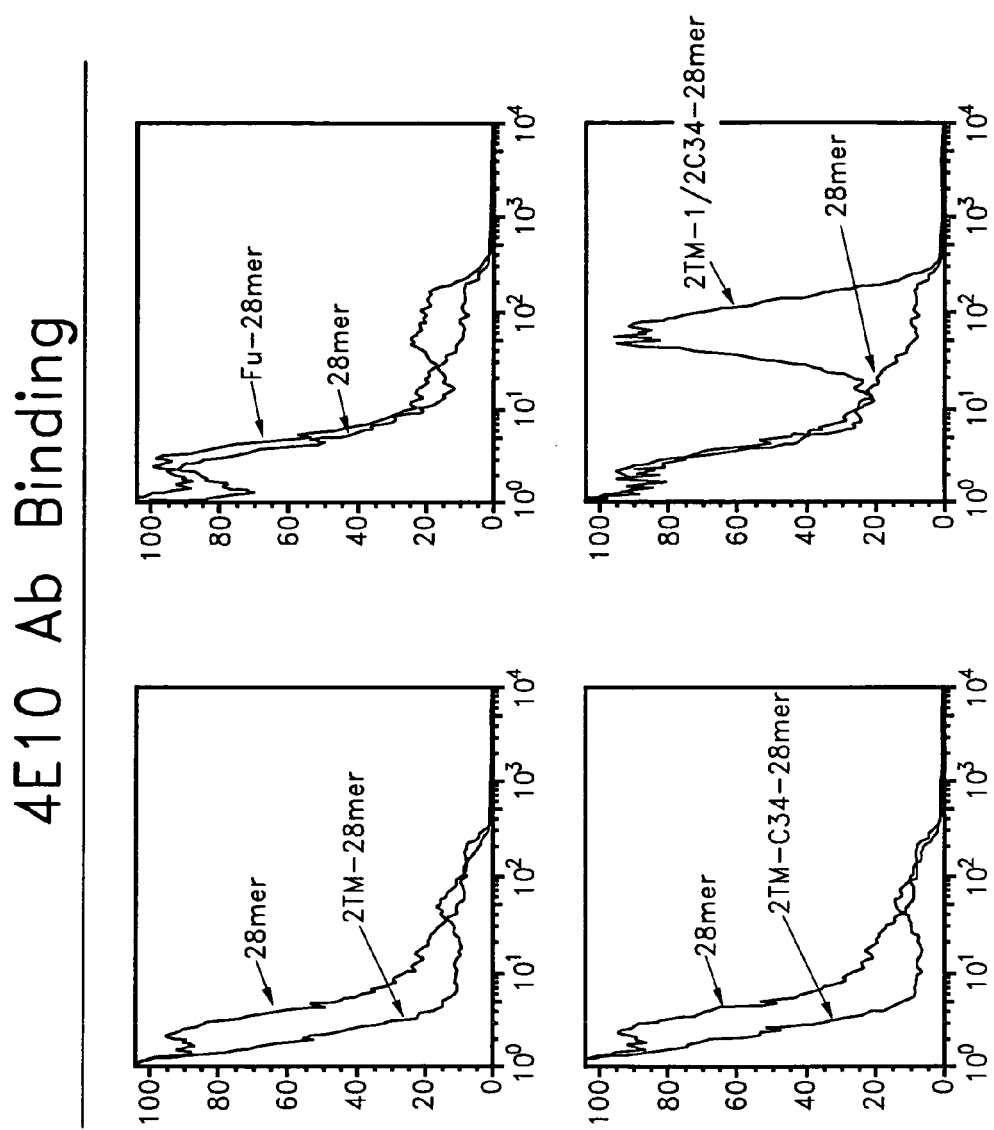

Hydrophobic CD4-TM or fusion peptide (FP) residues were added to the five-prime to the 28mer to potentially enhance lipid bilayer association. The C34 and ½ A C34 elements were added as spacers between the 28mer and the hydrophobic domain. The transient expression of the 2F5 epitopes by a set of variant gp41MPR constructs was examined by FACS analysis (FIG. 12). The data demonstrate the 2F5 antibody binding is enhanced when the epitope is expressed in the context of Fu-28mer and 2™-½C34-28mer, indicating either increased expression or an increase in 2F5 binding affinity. The transient expression of the 4E10 epitope by a set of variant MPR constructs was analyzed by FACS analysis (FIG. 13). The data demonstrate that, similar to 2F5, 4E10 antibody binding is enhanced when the epitope is expressed in the context of Fu-28mer and 2™-½C34-28mer, indicating either increased expression or an increase in 4E10 binding affinity.

What is claimed is:

1. An isolated peptide that comprises at least ten contiguous amino acids of the sequence EKNEQELLELDK-WASLW (SEQ ID NO: 1) and that binds to monoclonal antibody 2F5, wherein (i) the isolated peptide is conformationally stabilized to provide a three dimensional structure that corresponds to that of SEQ ID NO: 1 when complexed with the 2F5 antibody, (ii) the isolated peptide comprises a face that does not bind to the 2F5 antibody, and (iii) the isolated peptide is associated with a lipid.

2. An isolated peptide of claim 1, wherein the face that does not bind to the 2F5 antibody is occluded with appended groups.

3. An isolated peptide of claim 2, wherein the appended groups are carbohydrate moieties.

4. An isolated peptide of claim 1, wherein the peptide is conformationally stabilized with a linkage selected from the group consisting of a disulfide bond and a lactam bridge.

5. The isolated peptide of claim 1, wherein lipid is a phospholipid not normally found on the outer cytoplasmic membrane of human cells.

6. The isolated peptide of claim 1, wherein the lipid is in the form of a proteoliposome.

7. A method of generating a humoral immune response against a human immunodeficiency virus type 1 (HIV-1) gp41 envelope glycoprotein in a mammal, which method comprises (a) preparing a composition comprising the isolated peptide of claim and a pharmaceutically acceptable carrier, and (b) administering the composition to a mammal, whereupon a humoral immune response is generated against the HIV-1 gp41 envelope glycoprotein in the mammal.

\* \* \* \* \*

SEQUENCE LISTING

<160> NUMBER OF SEQ ID NOS: 30

<210> SEQ ID NO 1
<211> LENGTH: 17
<212> TYPE: PRT
<213> ORGANISM: HIV-1

<400> SEQUENCE: 1

Glu Lys Asn Glu Gln Glu Leu Leu Glu Leu Asp Lys Trp Ala Ser Leu
1               5                   10                  15

Trp

<210> SEQ ID NO 2
<211> LENGTH: 6
<212> TYPE: PRT
<213> ORGANISM: HIV-1

<400> SEQUENCE: 2

Asn Trp Phe Asn Ile Thr
1               5

```
<210> SEQ ID NO 3
<211> LENGTH: 6
<212> TYPE: PRT
<213> ORGANISM: HIV-1

<400> SEQUENCE: 3

Glu Leu Asp Lys Ile Ser
 1               5

<210> SEQ ID NO 4
<211> LENGTH: 12
<212> TYPE: PRT
<213> ORGANISM: HIV-1

<400> SEQUENCE: 4

Glu Leu Leu Glu Leu Asp Lys Ile Ser Leu Trp Asn
 1               5                  10

<210> SEQ ID NO 5
<211> LENGTH: 18
<212> TYPE: PRT
<213> ORGANISM: HIV-1

<400> SEQUENCE: 5

Asn Glu Gln Glu Leu Leu Glu Leu Asp Lys Ile Ser Leu Trp Asn Trp
 1               5                  10                  15

Phe Asp

<210> SEQ ID NO 6
<211> LENGTH: 8
<212> TYPE: PRT
<213> ORGANISM: HIV-1

<400> SEQUENCE: 6

Leu Glu Leu Asp Lys Ile Ser Leu
 1               5

<210> SEQ ID NO 7
<211> LENGTH: 10
<212> TYPE: PRT
<213> ORGANISM: HIV-1

<400> SEQUENCE: 7

Leu Leu Glu Leu Asp Lys Ile Ser Leu Trp
 1               5                  10

<210> SEQ ID NO 8
<211> LENGTH: 16
<212> TYPE: PRT
<213> ORGANISM: Homo sapiens

<400> SEQUENCE: 8

Ser Gly Thr Ala Ser Val Val Cys Leu Leu Asn Asn Phe Tyr Pro Arg
 1               5                  10                  15

<210> SEQ ID NO 9
<211> LENGTH: 15
<212> TYPE: PRT
<213> ORGANISM: Homo sapiens

<400> SEQUENCE: 9

Ser Gly Thr Ala Ser Trp Cys Leu Leu Asn Asn Phe Tyr Pro Arg
 1               5                  10                  15

<210> SEQ ID NO 10
```

```
<211> LENGTH: 22
<212> TYPE: PRT
<213> ORGANISM: Homo sapiens

<400> SEQUENCE: 10

Gly Pro Val Asn Ala Met Asp Val Trp Gly Gln Ile Thr Val Thr Ile
 1               5                  10                  15

Ser Ser Thr Ser Thr Lys
            20

<210> SEQ ID NO 11
<211> LENGTH: 4
<212> TYPE: PRT
<213> ORGANISM: HIV-1

<400> SEQUENCE: 11

Arg Glu Lys Arg
 1

<210> SEQ ID NO 12
<211> LENGTH: 4
<212> TYPE: PRT
<213> ORGANISM: Artificial Sequence
<220> FEATURE:
<223> OTHER INFORMATION: modified HIV-1 peptide

<400> SEQUENCE: 12

Ser Glu Lys Ser
 1

<210> SEQ ID NO 13
<211> LENGTH: 9
<212> TYPE: PRT
<213> ORGANISM: Artificial Sequence
<220> FEATURE:
<223> OTHER INFORMATION: C9 tag

<400> SEQUENCE: 13

Thr Glu Thr Ser Gln Val Ala Pro Ala
 1               5

<210> SEQ ID NO 14
<211> LENGTH: 27
<212> TYPE: PRT
<213> ORGANISM: HIV-1

<400> SEQUENCE: 14

Asn Glu Gln Glu Leu Leu Glu Leu Asp Lys Ile Ser Leu Trp Asn Trp
 1               5                  10                  15

Phe Asp Ile Thr Asn Trp Leu Trp Tyr Ile Lys
            20                  25

<210> SEQ ID NO 15
<211> LENGTH: 13
<212> TYPE: PRT
<213> ORGANISM: HIV-1

<400> SEQUENCE: 15

Asn Glu Gln Glu Leu Leu Glu Leu Asp Lys Ile Ser Leu
 1               5                  10

<210> SEQ ID NO 16
<211> LENGTH: 14
<212> TYPE: PRT
<213> ORGANISM: HIV-1
```

-continued

```
<400> SEQUENCE: 16

Trp Asn Trp Phe Asp Ile Thr Asn Trp Leu Trp Tyr Ile Lys
1               5                   10

<210> SEQ ID NO 17
<211> LENGTH: 24
<212> TYPE: PRT
<213> ORGANISM: HIV-1

<400> SEQUENCE: 17

Asn Glu Gln Glu Leu Leu Glu Leu Asp Lys Ile Ser Leu Trp Asn Trp
1               5                   10                  15

Phe Asp Ile Thr Asn Trp Leu Trp
            20

<210> SEQ ID NO 18
<211> LENGTH: 9
<212> TYPE: PRT
<213> ORGANISM: Homo sapiens

<400> SEQUENCE: 18

Tyr Pro Tyr Asp Val Pro Asp Tyr Ala
1               5

<210> SEQ ID NO 19
<211> LENGTH: 6
<212> TYPE: PRT
<213> ORGANISM: HIV-1

<400> SEQUENCE: 19

Glu Leu Asp Lys Trp Ala
1               5

<210> SEQ ID NO 20
<211> LENGTH: 28
<212> TYPE: PRT
<213> ORGANISM: HIV-1

<400> SEQUENCE: 20

Asn Glu Gln Glu Leu Leu Glu Leu Asp Lys Trp Ala Ser Leu Trp Asn
1               5                   10                  15

Trp Phe Asn Ile Thr Asn Trp Leu Trp Tyr Ile Lys
            20                  25

<210> SEQ ID NO 21
<211> LENGTH: 291
<212> TYPE: DNA
<213> ORGANISM: Homo sapiens

<400> SEQUENCE: 21
aggatcacgt taaaggaatc gggtcctccg ctggtgaaac ccacacagac tctcacgctg    60
acctgttcct tctctgggtt ctcactgtcc gattttggag tgggtgtggg ctggatccgt   120
cagcccccag aaaggccct agagtggctt gcaatcattt attcggatga tgataagcgc   180
tacagcccat cgctgaacac cagactcacc atcaccaagg acacctccaa aaatcaagtt   240
gtccttgtca tgactagggt gagtcctgtg acacagcca cgtatttctg t             291

<210> SEQ ID NO 22
<211> LENGTH: 291
<212> TYPE: DNA
<213> ORGANISM: Homo sapiens

<400> SEQUENCE: 22
```

```
cagatcacct tgaaggagtc tggtcctacg ctggtgaaac ccacacagac cctcacgctg       60
acctgcacct tctctgggtt ctcactcagc actagtggag tgggtgtggg ctggatccgt      120
cagcccccag gaaaggccct ggagtggctt gcactcattt attgggatga tgataagcgc      180
tacagcccat ctctgaagag caggctcacc atcaccaagg acacctccaa aaaccaggtg      240
gtccttacaa tgaccaacat ggaccctgtg gacacagcca catattactg t               291

<210> SEQ ID NO 23
<211> LENGTH: 291
<212> TYPE: DNA
<213> ORGANISM: Homo sapiens

<400> SEQUENCE: 23
cagatcacct tgaaggagtc tggtcctacg ctggtgaaac ccacacagac cctcacgctg       60
acctgcacct tctctgggtt ctcactcagc actagtggag tgggtgtggg ctggatccgt      120
cagcccccag gaaaggccct ggagtggctt gcactcattt attgggatga tgataagcgc      180
tacggcccat ctctgaagag caggctcacc atcaccaagg acacctccaa aaaccaggtg      240
gtccttacaa tgaccaacat ggaccctgtg gacacagcca catattactg t               291

<210> SEQ ID NO 24
<211> LENGTH: 291
<212> TYPE: DNA
<213> ORGANISM: Homo sapiens

<400> SEQUENCE: 24
cagatcacct tgaaggagtc tggtcctacg ctggtgaaac ccacacagac cctcacgctg       60
acctgcacct tctctgggtt ctcactcagc actagtggag tgggtgtggg ctggatccgt      120
cagcccccag gaaaggccct ggagtggctt gcactcatttt attggaatga tgataagcgc     180
tacagcccat ctctgaagag caggctcacc atcaccaagg acacctccaa aaaccaggtg      240
gtccttacaa tgaccaacat ggaccctgtg gacacagcca catattactg t               291

<210> SEQ ID NO 25
<211> LENGTH: 291
<212> TYPE: DNA
<213> ORGANISM: Homo sapiens

<400> SEQUENCE: 25
caggtcacct tgaaggagtc tggtcctacg ctggtgaaac ccacacagac cctcacgctg       60
acctgcacct tctctgggtt ctcactcagc actagtggag tgggtgtggg ctggatccgt      120
cagcccccag gaaaggccct ggagtggctt gcactcatttt attgggatga tgataagcgc     180
tacggcccat ctctgaagag caggctcacc atcaccaagg acacctccaa aaaccaggtg      240
gtccttacaa tgaccaacat ggaccctgtg gacacagcca catattactg t               291

<210> SEQ ID NO 26
<211> LENGTH: 291
<212> TYPE: DNA
<213> ORGANISM: Homo sapiens

<400> SEQUENCE: 26
cagatcacct tgaaggagtc tggtcctacg ctggtgaaac ccacacagac cctcacgctg       60
acctgcacct tctctgggtt ctcactcagc actagtggag tgggtgtggg ctggatccgt      120
cagcccccag gaaaggccct ggagtggctt gcactcattt attggaatga tgataagcgc      180
tacagcccat ctctgaagag caggctcacc atcaccaagg acacctccaa aaaccaggtg      240
```

```
gtccttacaa tgaccaacat ggaccctgtg gacacaggca catattactg t           291
```

```
<210> SEQ ID NO 27
<211> LENGTH: 60
<212> TYPE: PRT
<213> ORGANISM: HIV-1

<400> SEQUENCE: 27

Asn His Thr Thr Trp Met Glu Trp Asp Arg Glu Ile Asn Asn Tyr Thr
1               5                   10                  15

Ser Leu Ile His Ser Leu Ile Glu Glu Ser Gln Asn Gln Gln Glu Lys
            20                  25                  30

Asn Glu Gln Glu Leu Leu Glu Leu Asp Lys Trp Ala Ser Leu Trp Asn
        35                  40                  45

Trp Phe Asp Ile Thr Asn Trp Leu Trp Tyr Ile Lys
    50                  55                  60

<210> SEQ ID NO 28
<211> LENGTH: 42
<212> TYPE: PRT
<213> ORGANISM: HIV-1

<400> SEQUENCE: 28

Asn His Thr Thr Trp Met Glu Trp Asp Arg Glu Ile Asn Asn Tyr Thr
1               5                   10                  15

Ser Leu Ile His Ser Leu Ile Glu Glu Ser Gln Asn Gln Gln Glu Lys
            20                  25                  30

Asn Glu Gln Glu Leu Leu Glu Leu Asp Lys
        35                  40

<210> SEQ ID NO 29
<211> LENGTH: 17
<212> TYPE: PRT
<213> ORGANISM: HIV-1

<400> SEQUENCE: 29

Glu Lys Asn Glu Gln Glu Leu Leu Glu Leu Asp Lys Trp Ala Ser Leu
1               5                   10                  15

Trp

<210> SEQ ID NO 30
<211> LENGTH: 19
<212> TYPE: PRT
<213> ORGANISM: HIV-1

<400> SEQUENCE: 30

Lys Trp Ala Ser Leu Trp Asn Trp Phe Asp Ile Thr Asn Trp Leu Trp
1               5                   10                  15

Tyr Ile Lys
```